(12) United States Patent
Metting et al.

(10) Patent No.: US 10,983,044 B2
(45) Date of Patent: Apr. 20, 2021

(54) DEVICE, SYSTEM AND METHOD FOR IN-SITU OPTICAL MONITORING AND CONTROL OF EXTRACTION AND PURIFICATION OF PLANT MATERIALS

(71) Applicant: Arometrix, Inc., Rockville, MD (US)

(72) Inventors: Christopher J. Metting, Germantown, MD (US); Jonathan K. Bunn, Germantown, MD (US); Timothy G. Collins, Union Beach, NJ (US); Hasso Von Bredow, Fairfax, VA (US); George Atanasoff, Washington, DC (US)

(73) Assignee: Arometrix, Inc., Rockville, MD (US)

( * ) Notice: Subject to any disclaimer, the term of this patent is extended or adjusted under 35 U.S.C. 154(b) by 12 days.

(21) Appl. No.: 16/018,935

(22) Filed: Jun. 26, 2018

(65) Prior Publication Data
US 2018/0306708 A1 Oct. 25, 2018

(51) Int. Cl.
| | |
|---|---|
| *G01N 21/25* | (2006.01) |
| *G01N 33/00* | (2006.01) |
| *C11B 3/12* | (2006.01) |
| *B01D 11/02* | (2006.01) |
| *B01D 3/42* | (2006.01) |
| *G01N 21/85* | (2006.01) |
| *C11B 1/00* | (2006.01) |

(Continued)

(52) U.S. Cl.
CPC ......... *G01N 21/255* (2013.01); *B01D 1/0082* (2013.01); *B01D 1/0088* (2013.01);
(Continued)

(58) Field of Classification Search
CPC .. G01J 1/02; G01J 1/0204; G01J 1/022; G01J 1/0271; G01J 1/04; G01J 1/0403;
(Continued)

(56) References Cited

U.S. PATENT DOCUMENTS

| | | | | |
|---|---|---|---|---|
| 2,841,849 A | | 7/1958 | Rice et al. | |
| 3,358,148 A | * | 12/1967 | Conklin | G01N 21/532 356/341 |
| 3,403,555 A | * | 10/1968 | Versaci | A61B 5/0275 73/861.05 |
| 4,025,311 A | * | 5/1977 | Bochinski | G01N 35/00 422/67 |

(Continued)

FOREIGN PATENT DOCUMENTS

JP 2002-267595 9/2002

OTHER PUBLICATIONS

International Search Report dated Apr. 15, 2019, issued in PCT counterpart application (No. PCT/US2019/016646).
(Continued)

*Primary Examiner* — Gordon J Stock, Jr.
(74) *Attorney, Agent, or Firm* — Womble Bond Dickinson (US) LLP

(57) ABSTRACT

In-situ optical spectroscopic monitoring, characterization and feedback control of extraction and purification processes of compounds such as oils, alkaloids, flavonoids, terpenes and cannabinoids derived from plant material are described. Liquids from an extraction or purification process flow down an optically transparent tube, such as one made of glass. An in-situ optical monitoring assembly is configured to be mounted onto the tube to measure optical properties of the liquid extract or liquid condensate as it flows in the tube. Optical properties of the flowing liquid may include optical transmittance, reflectance, photoluminescence, scattering, absorbance, turbidity, nephelometry, polarimetry and colorimetry. The output of the optical monitoring assembly can be used to display spectral and other about the flowing liquid, set alarms to notify an operator of a predetermined condition such as a set point, and used to control extraction or purification process.

57 Claims, 22 Drawing Sheets

(51) Int. Cl.
| | |
|---|---|
| *C11B 9/02* | (2006.01) |
| *G01N 21/01* | (2006.01) |
| *B01D 5/00* | (2006.01) |
| *B01D 1/14* | (2006.01) |
| *B01D 1/00* | (2006.01) |
| *B01D 3/02* | (2006.01) |
| *G01J 1/02* | (2006.01) |
| *G01J 3/02* | (2006.01) |
| *G01N 21/64* | (2006.01) |
| *G01N 21/53* | (2006.01) |
| *G01N 21/05* | (2006.01) |

(52) U.S. Cl.
CPC ............... *B01D 1/14* (2013.01); *B01D 3/02* (2013.01); *B01D 3/42* (2013.01); *B01D 5/006* (2013.01); *B01D 11/0207* (2013.01); *B01D 11/0296* (2013.01); *C11B 1/00* (2013.01); *C11B 3/12* (2013.01); *C11B 9/025* (2013.01); *G01J 1/0271* (2013.01); *G01J 3/0291* (2013.01); *G01N 21/01* (2013.01); *G01N 21/85* (2013.01); *G01N 33/0098* (2013.01); *G01N 21/05* (2013.01); *G01N 21/251* (2013.01); *G01N 21/53* (2013.01); *G01N 21/645* (2013.01)

(58) Field of Classification Search
CPC ............... G01J 1/06; G01J 2001/0257; G01J 2001/0261; G01J 2001/0276; G01J 2001/063; G01J 3/0272; G01J 3/0291; G01J 3/42; G01J 3/427; G01J 3/46; G01J 3/02; G01J 3/0256; B01D 11/0207; B01D 11/0296; B01D 1/0082; B01D 1/0088; B01D 1/14; B01D 3/02; B01D 3/42; B01D 5/006; C11B 1/00; C11B 3/12; C11B 9/25; C11B 9/02; C11B 9/022; C11B 9/027; C11B 3/006; C11B 1/10; G01N 21/01; G01N 21/05; G01N 21/21; G01N 21/251; G01N 21/255; G01N 21/53; G01N 21/645; G01N 21/85; G01N 33/098; G01N 2021/0106; G01N 2021/0112; G01N 2021/052; G01N 2021/6473; G01N 2021/6491; G01N 2021/6495; G01N 2021/6497; G01N 21/09; G01N 21/17; G01N 2021/1734; G01N 2021/1736; G01N 2021/1738; G01N 2021/174; G01N 2021/14732; G01N 2021/1744; G01N 2021/4707; G01N 2021/4709; G01N 2021/4711; G01N 2021/4726; G01N 2021/4742; G01N 2021/4752; G01N 2021/4764; G01N 2021/4769; G01N 21/532; G01N 21/534; G01N 21/59; G01N 21/62; G01N 21/63; G01N 21/64; G01N 21/75; G01N 21/84; G01N 2021/6417; G01N 2021/6419; G01N 2021/6421; G01N 2021/6463; G01N 2021/6467; G01N 2021/8466; G01N 21/25; G01N 21/253; G01N 21/27; G01N 21/272; G01N 21/31; G01N 21/3577; G01N 21/41; G01N 21/4738; G01N 21/474; G01N 33/02; G01N 33/025; G01N 33/03; G01N 33/15
See application file for complete search history.

(56) References Cited

U.S. PATENT DOCUMENTS

| | | | | |
|---|---|---|---|---|
| 4,181,610 | A * | 1/1980 | Shintani | A61M 1/1692 210/321.6 |
| 4,344,429 | A * | 8/1982 | Gupton | A61M 5/365 250/204 |
| 4,528,635 | A | 7/1985 | Juodikis et al. | |
| 4,543,482 | A * | 9/1985 | Brenholdt | G01N 21/53 250/343 |
| 4,649,281 | A * | 3/1987 | Schmitt | B01D 17/0214 250/574 |
| 4,673,820 | A * | 6/1987 | Kamen | G06M 11/00 250/573 |
| 4,759,825 | A * | 7/1988 | Medvey | B01D 3/085 137/386 |
| 4,797,655 | A * | 1/1989 | Orndal | A61M 1/3626 340/521 |
| 5,002,539 | A * | 3/1991 | Coble | A61M 5/1689 604/253 |
| 5,192,509 | A * | 3/1993 | Surjaatmadja | G01N 1/38 422/75 |
| 5,331,958 | A * | 7/1994 | Oppenheimer | A61B 5/14535 356/39 |
| 5,427,920 | A * | 6/1995 | Berndt | G01N 21/253 356/339 |
| 5,680,111 | A * | 10/1997 | Danby | A61M 5/365 250/573 |
| 6,510,330 | B1 * | 1/2003 | Enejder | G01N 21/532 356/39 |
| 6,529,751 | B1 * | 3/2003 | Van Driel | A61M 1/3626 250/573 |
| 7,215,420 | B2 | 5/2007 | Gellerman et al. | |
| 7,339,671 | B2 * | 3/2008 | Peng | G01N 21/51 356/244 |
| 7,460,232 | B2 * | 12/2008 | Buijs | G01N 21/05 356/410 |
| 7,661,294 | B2 * | 2/2010 | Dam | A61M 1/3626 250/343 |
| 8,054,452 | B2 * | 11/2011 | Bado | A61B 5/14557 356/39 |
| 8,873,051 | B2 | 10/2014 | Kaduchak et al. | |
| 9,291,503 | B2 | 3/2016 | Takenaka et al. | |
| 9,915,600 | B2 | 3/2018 | Walls et al. | |
| 10,130,749 | B2 * | 11/2018 | Schade | A61M 1/367 |
| 10,281,437 | B2 * | 5/2019 | Leaders | G01N 29/024 |
| 10,758,839 | B1 | 9/2020 | Lantz | |
| 2005/0219526 | A1 * | 10/2005 | Peng | G01N 21/274 356/338 |
| 2005/0244953 | A1 | 11/2005 | Cohen | |
| 2008/0051732 | A1 * | 2/2008 | Chen | A61M 5/1689 604/253 |
| 2008/0094627 | A1 | 4/2008 | Oldham et al. | |
| 2008/0128261 | A1 * | 6/2008 | Balass | B01D 5/006 202/176 |
| 2010/0004518 | A1 | 1/2010 | Vo et al. | |
| 2010/0031743 | A1 | 2/2010 | Scheiner et al. | |
| 2012/0059303 | A1 | 3/2012 | Barrett et al. | |
| 2012/0281203 | A1 | 11/2012 | Hermansen | |
| 2013/0033697 | A1 * | 2/2013 | Zhang | G01N 21/05 356/39 |
| 2015/0300881 | A1 | 10/2015 | Takenaka et al. | |
| 2017/0252385 | A1 | 9/2017 | Jones | |
| 2018/0078874 | A1 * | 3/2018 | Thomas | B01D 53/18 |

OTHER PUBLICATIONS

Written Opinion dated Apr. 15, 2019, issued in PCT counterpart application (No. PCT/US2019/016646).
U.S. Appl. No. 62/619,931, filed Jan. 22, 2018, Lantz.

* cited by examiner

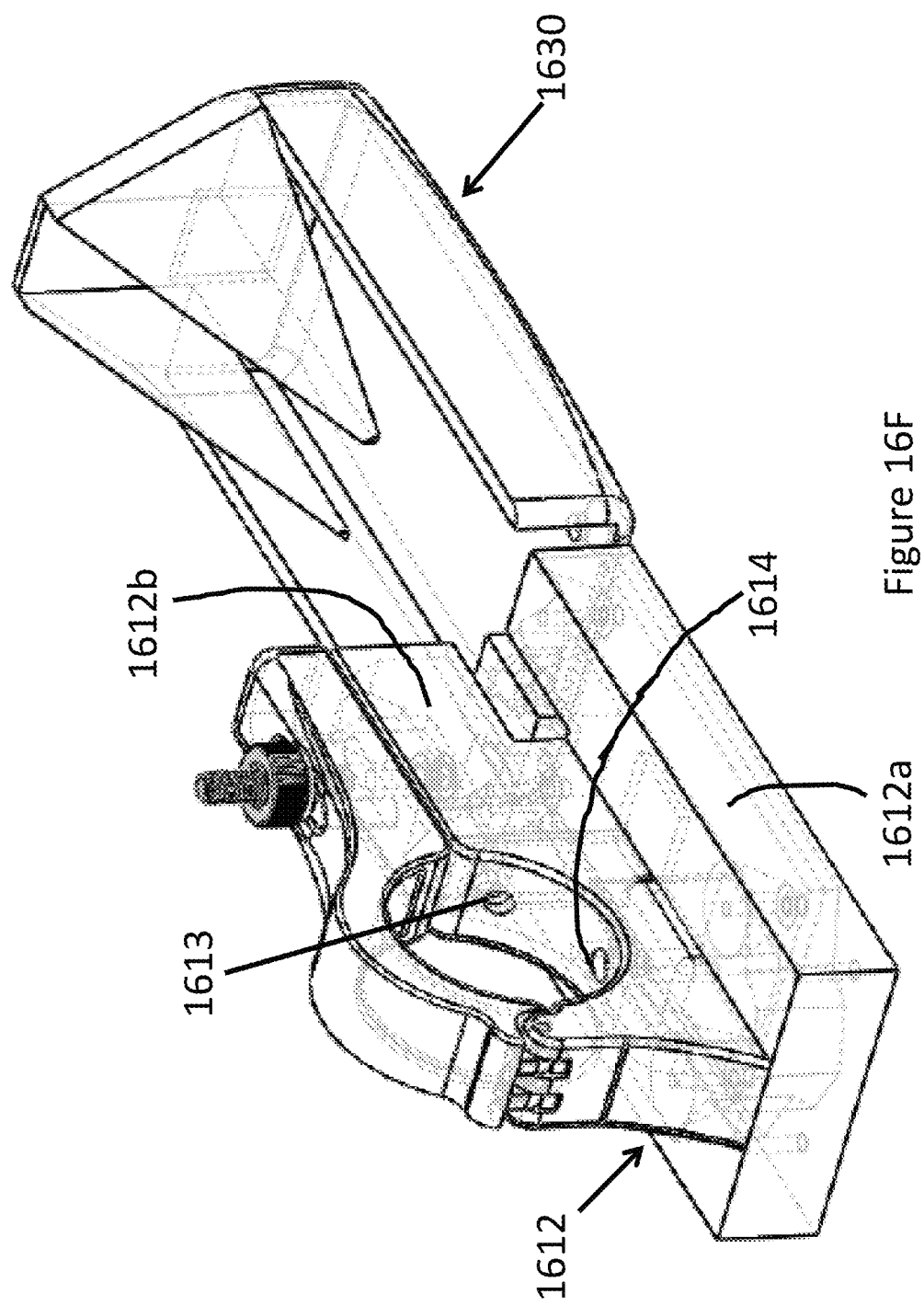

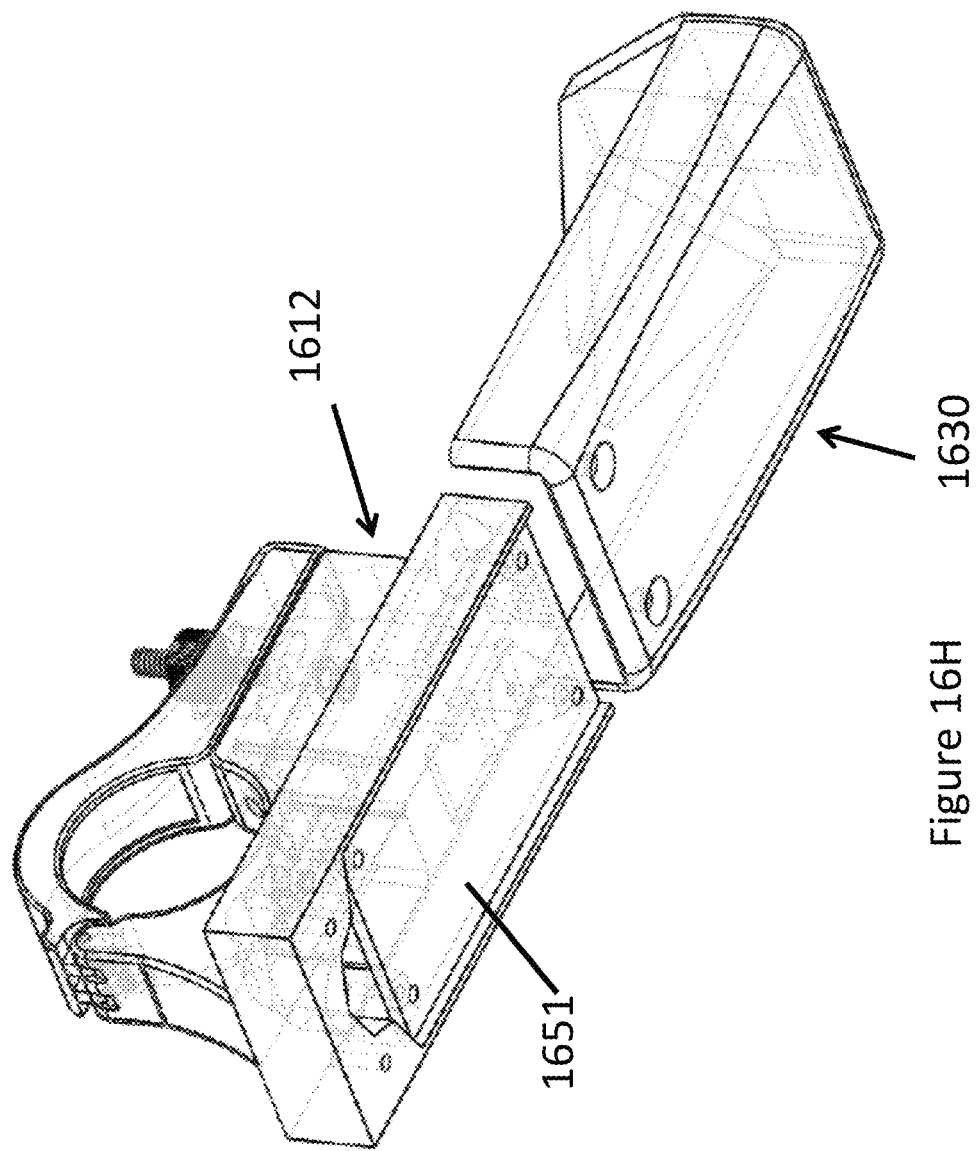

DEVICE, SYSTEM AND METHOD FOR IN-SITU OPTICAL MONITORING AND CONTROL OF EXTRACTION AND PURIFICATION OF PLANT MATERIALS

FIELD OF THE INVENTION

The present disclosure relates to methods and systems for in-situ monitoring of extraction and purification of chemical and bioactive compounds from plant and plant-like materials.

BACKGROUND OF THE INVENTION

The extracts from plant materials are a rich source of compounds used in many industries such as nutraceutical, pharmaceutical and therapeutic industries. Many of the phytochemicals from plants or plant-like sources have been reported to have an impact on human and animal health. For example, high content of flavonoids in medicinal plants have been associated with their antioxidant activities that play a role in the prevention of age-related diseases.

Plant materials include a varied group of plant parts from one or different/mixed plant species. Categories of plant material include, but not limited to, grass, flowers, herbs, rushes, barks, woods, gourds, stems, roots, nuts, acorns, bulbs, seeds, fruits, leaves, etc. Plant-like organisms are multicellular organisms that produce their own food by photosynthesis and have more or less rigid cell walls, such as algae and fungi. Plant-like materials such as seaweed and water moss are considered algae, while mushrooms, yeast and truffles are considered fungi.

An essential oil is a concentrated hydrophobic liquid containing volatile compounds from plants. Essential oils are also known as volatile oils, ethereal oils, or simply as the oil of the plant from which they were extracted, such as clove oil or cinnamon oil. Oil is "essential" in the sense that it contains the "essence" of the plant, i.e., the characteristic fragrance of the plant from which it is derived. Essential oils are widely used in numerous nutraceutical, pharmaceutical, cosmetic or therapeutic applications for millennia. Carrier oils, such as vegetable and herbal oil, are the "base" for the preparation of a huge array of products, such as food and nutraceutical products, cosmetic and medical creams, lotions, massage, facial and body oils, lubricants and gels, and salves. They are frequently used to dilute the essential oils before their use in the cosmetics and aromatherapy and are often referred as "base oils". Alkaloids, a group of naturally occurring nitrogen-containing compounds, produced predominantly by plants and fungi, and have pronounced biological effects on both humans and animals. For instance, morphine, quinine, strychnine, and nicotine are all naturally occurring alkaloids in flowering plants. Flavonoids, terpenes and terpenoids are aromatic organic compounds, such as quercetin, camphor, eucalyptol and menthol, mainly found as compounds in oils extracted from plants, and are well known for their medicinal and industrial use as psychoactive, antioxidant or painkiller drugs, flavors, fragrances and spices. *Cannabis* is a genus of plants that includes *Cannabis sativa, Cannabis indica* and *Cannabis ruderalis* and has long been used for its hemp fiber material, as milk, seeds and oils for medical and recreational purposes. Furthermore, multiple chemical and bioactive compounds are extracted from both algae and fungi and have effects on humans and animals, and are also included in many drugs or chemical products.

Extraction of plant compounds can be done by various extraction procedures, such as those disclosed in J. Azmur et al., J. Food Engineering, 117 (2013) 426-436. Maceration is a simple method, where the coarse or powdered plant material is soaked into the solvent in order to soften the material and break the plant cells to release the soluble phytochemicals. After the soaking period the mixture is pressed, filtered and/or boiled off to remove the solvent, leaving the extracted compound behind. Solvent extraction is a method for separation of compounds based on their relative solubility in different liquids, such as water (polar) or organic solvents (non-polar). For example, liquid propane gas or liquid carbon dioxide are some frequently used solvents for extraction of cannabinoids from the plant material. Cold pressing (also known as expression process) is an extraction method, where the plant material is subjected to mechanical pressure without application of external heat in order to preserve the sensitive plant compounds in the extract. Cold pressing is frequently used to extract compounds such as carrier and essential oils.

More sophisticated conventional extraction methods include the well-known Soxhlet method, described in Azwanida N N, Medicinal and Aromatic Plants, vol. 4, No. 3 (2015); (See FIG. 1). Generally, a small amount of the dry plant material is placed in a thimble, which is subsequently loaded into the Soxhlet extractor. The extraction solvent to be used is placed in a distillation flask and the flask is placed on the heating element. The Soxhlet extractor is placed atop the flask and a reflux condenser is placed atop the extractor.

The boiling temperature of the selected solvent to a large extend determines the type of compound extracted from the sample. The extraction procedure involves heating the solvent so that the solvent vapor travels up a distillation arm, and floods into the chamber housing the thimble of plant material. The condenser ensures that any solvent vapor cools, and drips back down into the chamber housing the solid material. The chamber containing the solid material slowly fills with warm solvent. Some of the desired compound dissolves in the warm solvent. When the Soxhlet chamber is almost full, the chamber is emptied by the siphon. The solvent is returned to the distillation flask. The thimble ensures that the rapid motion of the solvent does not transport any solid material to the still pot. This cycle may be allowed to repeat many times, over hours or days.

Another conventional method, very similar to the Soxhlet extractor, is the Kumagawa extractor, where the thimble is directly suspended inside the solvent flask above the boiling solvent. The thimble is surrounded by hot solvent vapor and maintained at a higher temperature compared to the Soxhlet extractor, thus allowing better extraction for compounds with higher melting temperatures.

Typically, the solvents used in such extraction process are hydrocarbon-based (i.e. liquid propane, alcohol, hexane, acetone), which have lower boiling temperatures than the compound to be extracted. More recently a supercritical $CO_2$ extraction process, as described in E. Reverchon et al., J. Agric. Food Chem. 43 6 (1995) 1654-1658, has been introduced, due to its low toxicity and environmental impact. The $CO_2$ extraction process claims to be a clean and safe method for extracting plants such as hops, *cannabis* and a wide range of nutraceuticals and organic crops.

Multiple non-conventional methods, which are more environmentally friendly due to decreased use of synthetic and organic chemicals, reduced operation time and better yield and quality of the extract, have been developed during the last 50 years. Ultrasound, pulsed electric field, extrusion, microwave and resistive heating and multiple others techniques have been used in one or another process as non-conventional methods.

Specific methods and extraction devices are also described in U.S. Pat. No. 9,789,147, whose contents are incorporated by reference.

Controlling the concentration and purity of the extracted compound directly in the extract as the extraction process is transpiring (in-situ) is a useful means to create a feedback process control, optimize the extraction process and improve the quality (i.e. potency) and safety of the product.

Frequently the essential oils and concentrates that get extracted from the plant can be contaminated with toxic chemicals, including heavy metals, microbes, pesticides and other hazardous compounds that get transferred from the original plant and further concentrated into the extract. For example, some *cannabis* farmers spray their plants with chemicals like avermectin, myclobutanil and bifenazate (See http://www.laweekly.com/news/*cannabis*-concentrates-have-a-problem-with-pesticides-7952469, retrieved Jun. 13, 2018). Exposure to these chemicals has been proven toxic or even carcinogenic. Even when the pesticides are undetectable on the plant itself, they frequently become concentrated during the extraction process, and the trace amounts are magnified. Strict guidelines are still to be imposed on the medical marijuana industry to ensure that the final product doesn't contain significant levels of heavy metals, aflatoxins, nitrates, pesticides or microbial contamination.

Therefore, controlling the quality of the extracted plant material is an important step in order to ensure public health. Specifically beneficial is the in-situ quality control during the extraction process, during which the concentration of these hazardous compounds increases and may exceed the allowable threshold. The in-situ monitoring and control plays the role of the first line of defense against contaminations. Furthermore, the timely information about a potential contamination, obtained as the extraction process is ongoing, can save time and energy and prevent contaminated material from reaching the subsequent steps of processing.

After the extraction process the obtained extract can contain multiple organic components such as oils, terpenes, alkaloids, chlorophylls, residual solvents and other phytomaterials. An additional purifying technique is needed to separate the different fractions and increase purity. Multiple purification techniques are developed and used, such as adsorption, filtration, centrifugal separation, etc.

Distillation is the major separation technique, and is used to further purify and concentrate the extracted product. Distillation is an evaporation technique used to isolate or purify various components present in the extract based on the difference in their vapor pressures. Therefore, with distillation, the separation is carried by differences in the volatility (boiling points), between the various compounds. For example, one of the distillation techniques, fractional distillation, separates the volatile oil in different fractions or portions at various vapor pressures in a fractionating vertical column, held at gradient temperatures. The vapors are allowed to condense at different temperatures; —the more volatile compounds condense at lower temperatures, while the less volatile compounds to condense in areas with higher temperatures. The process of fractional distillation is used to obtain the product in the purest form possible.

Fractional distillation is typically performed in large, vertical cylindrical columns known as 'distillation or fractionation towers' or 'distillation columns'. The distillation towers have liquid outlets at intervals up the column, which allow withdrawal of different fractions or products having different boiling points or boiling ranges. By increasing the temperature of the product inside the columns, the different volatile components are separated. The 'lightest' products (those with the lowest boiling point) exit from the top of the columns and the 'heaviest' products (those with the highest boiling point) exit from the bottom of the column.

For relatively small amounts of organic compound, other versions of a distillation process are used, such as steam distillation, where boiling water is passed through the raw material to drive out the volatile compounds. This method is frequently used for distillation of fragrances.

Another version of a distillation process is short-path distillation with its several modifications—Klugelrohr, Pope, etc. Instead of relying on natural separation of the fractions in a vertical column, these methods separate the fractions one after another by changing the temperature set points of the extract. At lower temperature set point fractions with lower boiling point are evaporated, then the temperature set point is raised and the next fraction is evaporated and so on. This method often deploys reduced pressure (rough to mid vacuum) and a condensing surface in close proximity to a heated evaporation surface (FIG. 2). For many applications low pressure and short distance to the heated evaporator presents some advantages as it results in better yield (less material loss), less thermal degradation of the compound and reduced distillation times. These techniques are especially preferred when the distillation compounds have greater molecular weight and are unstable at high temperatures.

Molecular distillation is a version of short-path distillation, where the distance between the evaporator and the condenser tube is even smaller than the traditional short-path distillation (2-3 cm) and the pressure approaches high vacuum values ($\sim 10^{-3}$ Torr). At these conditions the mean free path of the evaporated particles approaches the characteristic distance between the evaporator and the condenser. The amount of collisions between the particles inside the tube is minimal; —the molecular fluid is in a regime of free molecular flow. These conditions are beneficial for distillation and purification of very complex and thermally sensitive molecules such as vitamins and polyunsaturated fatty acids.

The individual fractions are separated by changing the temperature set point and subjective determination of the end point. Once the operator judges that a certain fraction is already evaporated, he/she manually switches the collection pot, raises the temperature and begins the separation of the next fraction. The moment when this operation is performed is frequently a matter of experience and art. The judgment is also highly susceptible to quality of the feedstock, which is often inconsistent. Results of these arbitrary actions are reduced product yield and process productivity, reduced product purity and/or contaminated products.

In the example of *cannabis*, often the extracted material is in a range of 55-70% cannabinoid, and it is typical to purify it up to a range from 85% to over 90%. The increased cannabinoid purity results in a product that is very light yellow in color, with high clarity and transparency. High fogginess, turbidity, stronger colorization or drift from the light yellow color are all signs of reduced quality.

An increasing number of small players and producers continue to enter the market of chemical compound extraction and purification of essential oils, terpenes and cannabinoids for both medical and recreational use, there is an increasing need for objective process control for non-destructive process monitoring, characterization and feedback process control. Furthermore, as the regulation authorities such as FDA, EPA and others continue to develop means to regulate and control the production of these and similar compounds from plant material, the role of the in-situ process control and product quality certification directly at the location of the producer becomes increasingly important.

SUMMARY

Generally, the subject matter of the present application is directed to devices, systems and methods for in-situ optical monitoring of extraction and purification of chemical compounds derived from plants and plant-like materials.

In-Situ Optical Monitoring Assembly

In one aspect, the subject matter of the present application is directed to an in-situ optical monitoring assembly configured to fit onto an optically transparent tube having liquid passing therethrough, the in-situ optical monitoring assembly comprising:

a body having one or more surfaces which conform to a contour of an optically transparent tube;

first and second optically transparent windows formed in the one or more surfaces; and first and second optical components mounted within the body and positioned at the first and second windows, respectively, such that direct line of sight is provided between each of the first and second optical components and an exterior of the body, through respective first and second windows.

The in-situ optical monitoring assembly may include any combination of the following features:

(a1) The body may comprise:
  a first bracket having a first concave surface which conforms to a contour of an optically transparent tube; and
  a second bracket having a second concave surface which conforms to a contour of an optically transparent tube; and
  the assembly is adjustable between:
    an open state in which the first and second concave surfaces do not face each other; and
    a closed state in which the first and second concave surfaces face each other.

(a2) the first and second windows are both formed in the first concave surface portion, and are circumferentially spaced apart from one another by a first angular distance.

(a3) The first optical component is a light source positioned at the first window; and
  the second optical component is a first light detector component positioned at the second window.

(a4) The first light detector component is an optical spectrometer mounted in the first bracket.

(a5) The second window is elongated in a circumferential direction of the first concave surface; and
  the first light detector component is configured to be repositioned along a length of the first concave surface so that light may be detected at variable angles of incidence through the elongated window.

(a6) The first and second optical components are passive optical components
  the first optical component is connected via a first fiber optics cable to a remotely located light source;
  the second optical component is connected via a first fiber optics cable to a remotely located first light detector component.

(a7) The first optical component comprises a first fiber optics cable having a first end terminating at the first window and configured to emit light directly through said first window, a second end of the first fiber optics cable being connected to a remotely located first light source; and
  the second optical component comprises a second fiber optics cable having a first end terminating at the second window and configured to directly collect light entering through the second window, a second end of the second fiber optics cable being connected to a remotely located first light detector component.

(a8) A third window formed in the first concave surface portion and circumferentially spaced apart from the first window by a second angular distance which is larger than the first angular distance; and
  a third optical component mounted within the body and positioned at the third window; wherein:
  the first optical component is a first light source positioned at the first window;
  the second optical component is a first light detector component positioned at the second window; and
  the third optical component is a second light detector component positioned at the third window.

(a9) At least one of the first and second light detectors is an optical spectrometer mounted in the first bracket.

(a10) A third window formed in the first concave surface portion and circumferentially spaced apart from the first window by a second angular distance which is larger than the first angular distance; and
  a third optical component mounted within the body and positioned at the third window; wherein:
  the first optical component is a first light source positioned at the first window;
  the second optical component is a first light detector component positioned at the second window; and
  the third optical component is a second light source positioned at the third window.

(a11) The first light detector is an optical spectrometer mounted in the first bracket.

(a12l) The first bracket houses a light source, a first light detector component, and an optical control circuit configured to control operation of the light source and the first light detector component.

(a13) The first bracket also houses a second light detector component comprising a photodetector.

(a14) A connector I provided on a surface of the first bracket.

(a15) The first bracket further comprises:
  a housing having a housing base portion on top of which is a narrower housing upper portion; and
  a base cover slidably mounted to the housing base.

(a16) A hinge connecting a first end of the first bracket to a first end of the second bracket; and
  a fastener configured to secure the first bracket to the second bracket in the closed state of the assembly, the fastener being located on a side of the brackets which is opposite from the hinge.

(a17) Each of the first and second concave surface portions subtends an angle of about 180°; and
  in a closed state of the assembly, the first and second concave surface portions together form a nearly continuous 360° cylindrical surface.

(a18) The body comprises a single bracket comprising a resilient material having a radially inner arcuate surface subtending more than 180° and less than 210°;
  the windows are formed on the inner surface at spaced apart locations along the arcuate inner surface; and
  the bracket is configured to expand in the outward radial direction when pressed against an optically transparent tube, resulting in the arcuate inner surface also expanding and allowing the bracket to snap onto the optically transparent tube.

(a19) The body comprises a single bracket having a radially inner arcuate surface subtending 360°;
the windows are formed on the inner surface at spaced apart locations along the arcuate inner surface;
the bracket is configured to be mounted over an end of an optically transparent tube.

(a20) The body comprises three or more brackets connected to one another.

In-Situ Optical Monitoring System

In another aspect, the subject matter of the present application is directed to an in-situ optical monitoring system configured to monitor a liquid flowing in an optically transparent tube, the system comprising:
the in-situ optical monitoring assembly described above;
an optical control circuit configured to control operation of at least one of the optical components; and
a computer and display integrated into a single unit, the computer configured to control the optical control circuit.

In the in-situ optical monitoring system, the first optical component may be a light source, the second optical component may be a first light detector component; and the light source, the first light detector component and the optical control circuit are all integrated into the in-situ optical monitoring assembly.

In the in-situ optical monitoring system, the first optical component may be a light source, the second optical component may be a first light detector component, and the optical control circuit may be integrated into the single unit, along with the computer and the display, and the single unit is connected to the in-situ optical monitoring assembly via fiber optics cables.

In any of the foregoing in-situ monitoring systems, the display may be a touch screen display configured to provide a process control interface to monitor and control an extraction and/or purification process.

In any of the foregoing in-situ monitoring systems, the in-situ monitoring assembly may include various combinations of features (a1)-(a20) described above.

In-Situ Methods

In yet another aspect, the subject matter of the present application is directed to an in-situ method of optically monitoring and/or controlling extraction or purification of a liquid obtained from plant material while the liquid flows in an optically transparent tube towards a collection vessel in which the liquid is collected, the method comprising:
mounting the in-situ optical monitoring assembly described above onto the optically transparent tube such that:
the optically transparent tube is at least partially nested in said one or more surfaces which conform to the contour of the optically transparent tube; and
the first and second optical components are in direct view of the flowing liquid;
illuminating, via the first optical component, the flowing liquid; and
detecting, via the second optical component, a first optical signal resulting from illuminating the flowing liquid.

The method may include any combination of the following features:

(m1) The optically transparent tube is tilted so that the liquid flows due to the effect of gravity.

(m2) The one or more surfaces which conform to the contour of the optically transparent tube are concave and encircle a length of the optical transparent tube.

(m3) In response to the first optical signal, issuing an alarm to an operator of equipment used in the extraction and/or purification.

(m4) In response to the first optical signal, determining at least one action to be taken to affect the extraction or purification process, the one or more actions may include (i) discontinuing collection of the liquid in the collection vessel, and/or (b) changing a temperature of a heating element configured to heat solvent during extraction of the liquid from the plant material.

(m5) The second optical component is a spectrometer located in the body of the in-situ monitoring assembly; and
the first optical signal is detected by the spectrometer; and
the method further comprises:
based on the first optical signal, sending spectral information from the in-situ monitoring assembly to a computer; and
in response to information in the spectral information, determining at least one action to be taken to affect the extraction or purification process.

(m6) The plant material is *cannabis*; and
the flowing liquid contains a cannabinoid bio-compound; and
the method comprises:
illuminating the cannabinoid bio-compound at one or more wavelengths in the range of 315 to 405 nm; and
detecting a photoluminescence response of the cannabinoid bio-compound in the flowing liquid in the range 405 to 800 nm.

(m7) With respect to feature (m6), Illuminating the cannabinoid bio-compound at a wavelength of 365 nm; and analyzing fluorescent light collected in the range of 410 nm to 450 nm.

(m8) A third optically transparent window formed in the one or more surfaces; and
a third optical component mounted within the body and positioned at the third windows such that direct line of sight is provided between the third optical component the flowing liquid, through the third window; wherein:
the third component is a light detector; and
the method further comprises:
receiving a second optical signal at the third optical component.

(m9) Detecting the first optical signal with a spectrometer located in the body of the in-situ monitoring assembly;
in response to detecting the first optical signal, sending spectral information from the in-situ monitoring assembly to a computer;
analyzing the spectral information to determine one or more of absorbance, turbidity, scattering, photoluminescence, nephelometric and polarimetric parameters, of the flowing liquid; and
in response to analyzing the spectral information, determining at least one action to be taken to affect the extraction or purification process.

(m10) With respect to feature (m9), the plant material is *cannabis;*
the flowing liquid contains a cannabinoid bio-compound; and
in response to the analyzed spectral information, discontinuing collection of the extracted or purified cannabinoid bio-compound in the collection vessel.

(m11) With respect to feature (m9), illuminating collected liquid which had accumulated in the collection vessel and detecting transmitted light which has passed through the collected liquid; obtaining colorimetric information from the transmitted light; and based on the colorimetric information, determining a quality of the collected liquid.

In any of the foregoing methods, the optical monitoring assembly which in mounted on the optically transparent tube may include various combinations of features (a1)-(a20) described above.

In still another aspect, the subject matter of the present application is directed to an in-situ method of optically monitoring and/or controlling extraction or purification of a liquid obtained from plant material while the liquid flows in an optically transparent tube towards a liquid collection vessel in which the liquid is collected, the method comprising:
  mounting onto the optically transparent tube, a device comprising at least first and second optical components and one or more surfaces which conform to the contour of the optically transparent tube, such that:
    the optically transparent tube is at least partially nested in said one or more surfaces of the device, and
    the first and second optical components are in direct view of the flowing liquid;
  illuminating, via the first optical component, the flowing liquid;
  detecting, via the second optical component, an optical signal resulting from illuminating the flowing liquid with the first optical component; and
  performing spectroscopic analysis of the optical signal to determine one or more of absorbance, turbidity, scattering, photoluminescence, nephelometric and polarimetric parameters, of the flowing liquid; and
  in response to said spectroscopic analysis, determining at least one action to be taken to affect the extraction or purification process, while the extraction and purification process continues.

In the above method, the optically transparent tube may be tilted so that the liquid flows due to the effect of gravity. Furthermore, the device which is mounted onto the optically transparent tube may include various combinations of features (a1)-(a20) described above.

The subject matter of the present application is also directed to in-situ optical spectroscopic monitoring, characterization and feedback control of extraction and purification processes of compounds such as oils, alkaloids, flavonoids, terpenes and cannabinoids derived from plant materials.

The subject matter of the present application is additionally directed to in-situ optical spectroscopic monitoring for detection of hazardous chemical compounds in the extract or in the distillate, such as presence of heavy metals, aflatoxins, nitrates, pesticides or microbial contamination.

The subject matter of the present application is further directed to in-situ quality monitoring and real time product characterization of plant extracts and distillates during the extraction and purification of the plant materials.

The subject matter of the present application is also directed to methods and systems for non-destructive optical spectroscopic monitoring, characterization and feedback process control performed directly at the processing equipment and concurrently with the extraction or purification/distillation processes without separation of an analyte from the in-line process.

BRIEF DESCRIPTION OF THE DRAWINGS

FIG. 16A-16H show details of an optical monitoring assembly in accordance with one embodiment of the subject matter of the present application.

DETAILED DESCRIPTION

Figure 1:
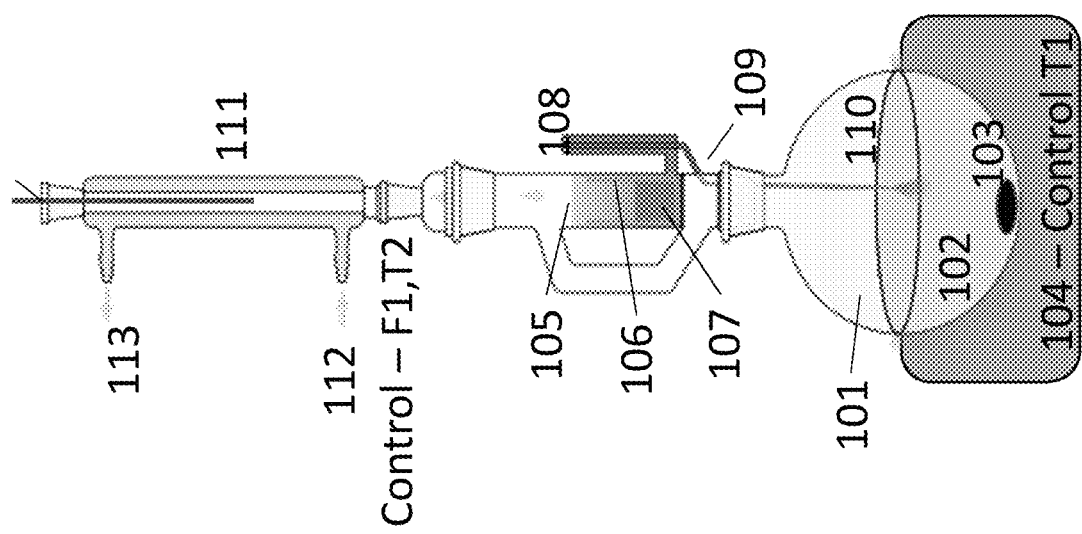
FIG. 1 shows the schematic of a typical Soxhlet extractor used in plant processing.

FIG. 1 shows the schematic of a typical prior art Soxhlet extractor used in plant processing. The source plant material 107 containing the bio-compound to be extracted is placed inside the thimble 106. The thimble 106 is loaded into the main chamber of the Soxhlet extractor 105. The extraction solvent 102 is placed in a distillation flask 101. The distillation flask is heated by the heating element 104 and stirred by the mechanical stirrer 103. The main chamber of the Soxhlet extractor 105 is placed atop the flask 101. A reflux condenser 111 is placed atop the extractor 105 and is cooled through coolant inlet 112 and coolant outlet 113. The coolant is typically water. The evaporated solvent 102 is condensed in the condenser 111 and fills the main chamber of the Soxhlet extractor 105 housing the thimble 106. The bio-compound 110 is dissolved from the plant material 107 by the solvent 102, fills the siphon up to the siphon top 108, and flows back into the flask 101 through the tilted siphon exit 109.

The siphon exit 109 comprises an optically transparent tube having a lumen therein, through which the bio-compound flows into the flask 101. Such an optically transparent tube may be formed of glass or some other chemically and optically suitable material so as to permit optical illumination and/or detection through its walls.

Figure 2:
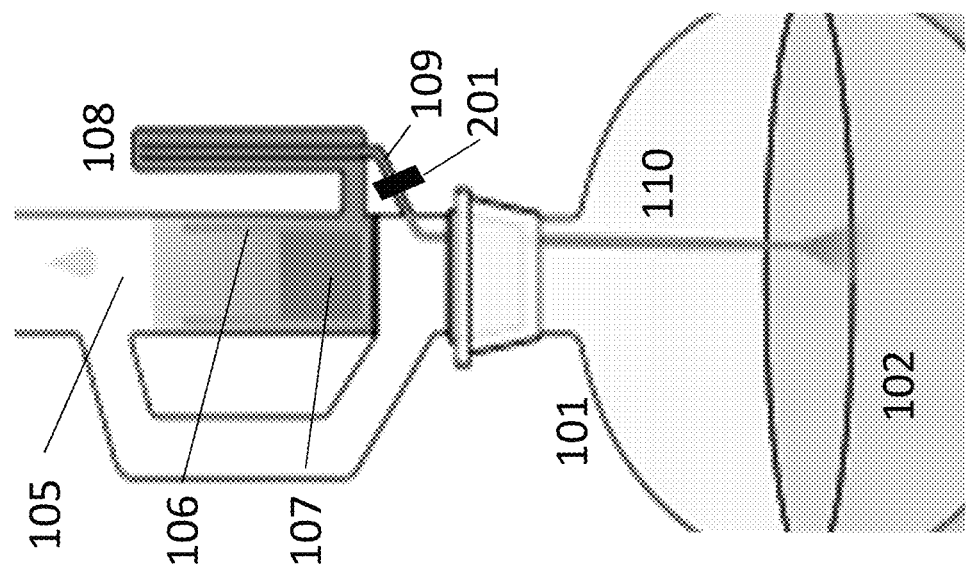
FIG. 2 shows an enlarged view of the extractor of FIG. 1, having an in-situ monitoring assembly installed.

FIG. 2 shows a magnified view of the extractor seen in FIG. 1, having an in-situ monitoring assembly 201 according to one aspect of the present invention. The optical monitoring assembly 201 is installed on the tilted siphon exit 109 and is aligned to optically monitor the flowing solvent 102 with dissolved bio-compound 110 therein, as it passes from the siphon 108 to the flask 101. The monitoring assembly can include a spectroscopic device such as a fluorometer, an absorbance monitor, a polarimeter, nephelometer/scatterometer or a turbidity meter, or combinations of these. Having a tilted (i.e., "non-horizontal") siphon exit 109 allows the flowing liquid to flow due to the effect of gravity, and having the siphon exit 109 tilted at angle well under 90° helps slows the flow of liquid so that the flowing liquid within the siphon exit 109 has an enhanced cross-sectional height which helps increase the strength of any detected optical signal.

Figure 3:
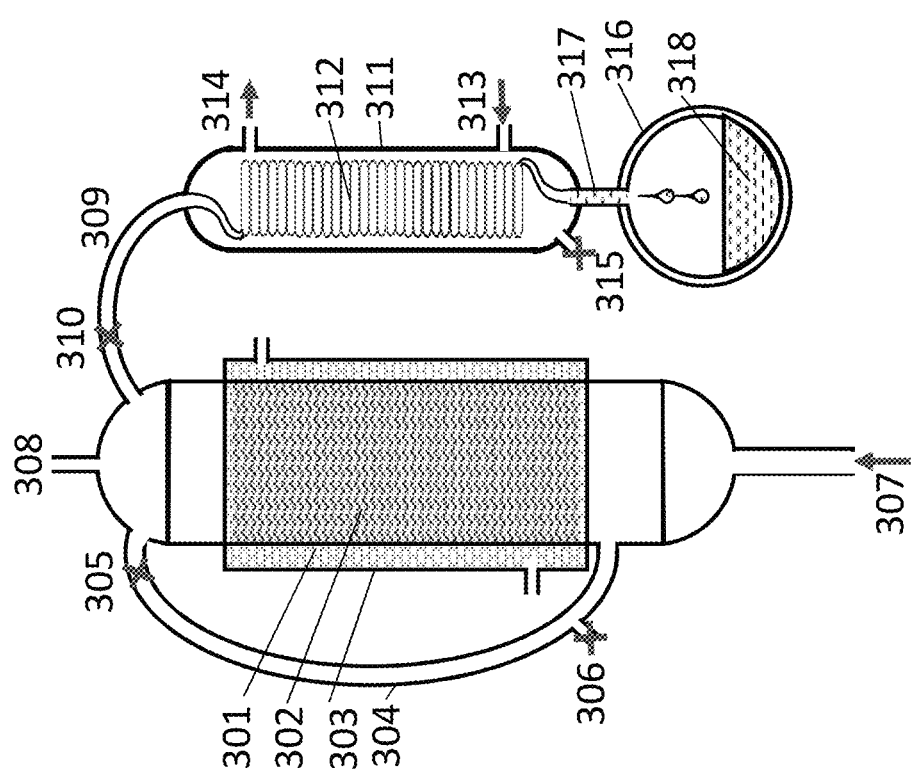
FIG. 3 shows the schematic of a typical small laboratory extractor used in plant processing.

FIG. 3 shows the schematic of another small laboratory extractor used in plant processing, which might be assembled from commercially available laboratory glassware. The extractor comprises a hollow cylindrical column 301 packed with raw plant extraction material 302, which might be mixed with inert matrix material such as glass beads. Column 301 is surrounded by a mantle 303 for heating or insulation to maintain the cylindrical column 301 at its operating temperature. In some embodiments, the column 301 is contained within an oven, which is maintained at a specific controlled temperature. The extractor further includes a recirculation pipe 304 fitted with a first controlling valve 305 and sampling outlet valve 306. A second outlet pipe 309 with a second controlling valve 310 feeds into the condenser assembly 311. The condenser assembly 311 comprises one or more condensers 312 and is cooled by coolant (typically water) entering the condenser 312 via the coolant inlet 313 and exiting the condenser 312 via the coolant outlet 314. The condenser assembly might also be supplied with a sample port 315. A collection vessel, such as a distillate collection flask 316 is attached to the condenser.

Heated gas is introduced to the extractor through gas inlet port 307. When the first controlling valve 305 is open, the gas 307 re-circulates through the column 301. When second controlling valve 310 is open, the gas enters the condenser 312 and the condensed liquid with dissolved bio-compound 318 flows through the flask inlet 317, into the distillate collection flask 316, and fills the bottom of the distillate collection flask 316.

Figure 4:
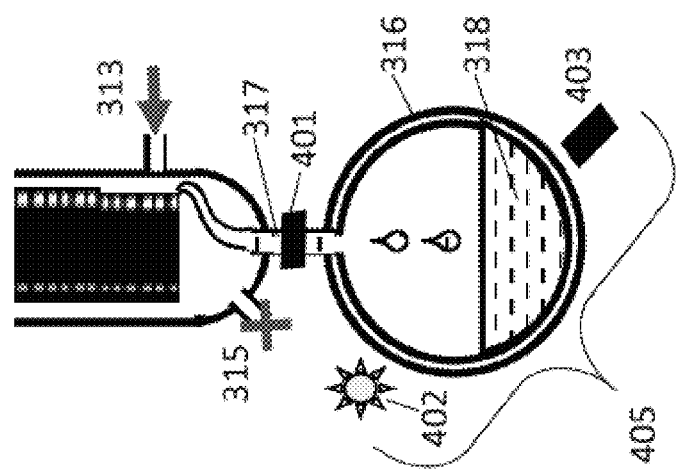
FIG. 4 shows an enlarged view of the extractor of FIG. 2, having an in-situ monitoring assembly installed.

FIG. 4 shows a magnified view of the extractor as per FIG. 3, having an in-situ optical monitoring assembly 401 in accordance with the subjection matter of the present application. The in-situ optical monitoring assembly 401 is installed on the flask inlet 317 and optically aligned to monitor the flowing liquid condensate with dissolved bio-compound 318 from the condenser assembly to the distillate collection flask 316. The flask inlet 317 is an optically transparent tube which is configured to permit optical illumination and/or detection through its walls. In one embodiment, the first in-situ optical monitoring assembly 401 is a fluorometer. In FIG. 4, the flask inlet 317 is shown to be vertically oriented (i.e., tilted at a 90° angle), and in the arrangement shown, the flowing liquid will adhere to the sides of the flask inlet 317 where the dissolved bio-compounds may be optically detected.

An auxiliary optical monitoring assembly 405 is optically aligned to monitor the condensed liquid with dissolved bio-compound 318 directly in the distillate collection flask 316. The auxiliary optical monitoring assembly 405 may include an illuminating optical component, such as a calibrated white light source 402 configured to illuminate the condensed liquid with dissolved bio-compound 318 and a receiving optical component, such as an optical spectroscopic component 403 optically aligned to receive the transmitted light from the condensed liquid with dissolved bio-compound 318. In one embodiment, the auxiliary optical monitoring assembly 405 comprises a colorimeter.

In one embodiment, the auxiliary optical monitoring assembly 405 may comprise a shroud surrounding the distillate collection flask 316 to prevent ambient light from entering the flask 316. For the spherical flask 316, the shroud may comprise first and second hemispherical shells which can be fitted together with the generally spherical flask 316 positioned in-between. The inner surface of each hemispherical shell conforms to the spherical contour of the flask. It is understood that shells having shapes other than hemispherical can be used with flasks of other shapes.

In some embodiments, the flask is optically transparent only at those discrete locations on its spherical surface where illumination and detection take place, the remainder of the spherical surface being, e.g., painted black to keep out unwanted ambient light. In such case, the auxiliary optical monitoring assembly 405 may comprise a ribbon-shaped unit encircling the distillate collection flask 316 and removably attached thereto by, e.g., clamping.

Figure 5:
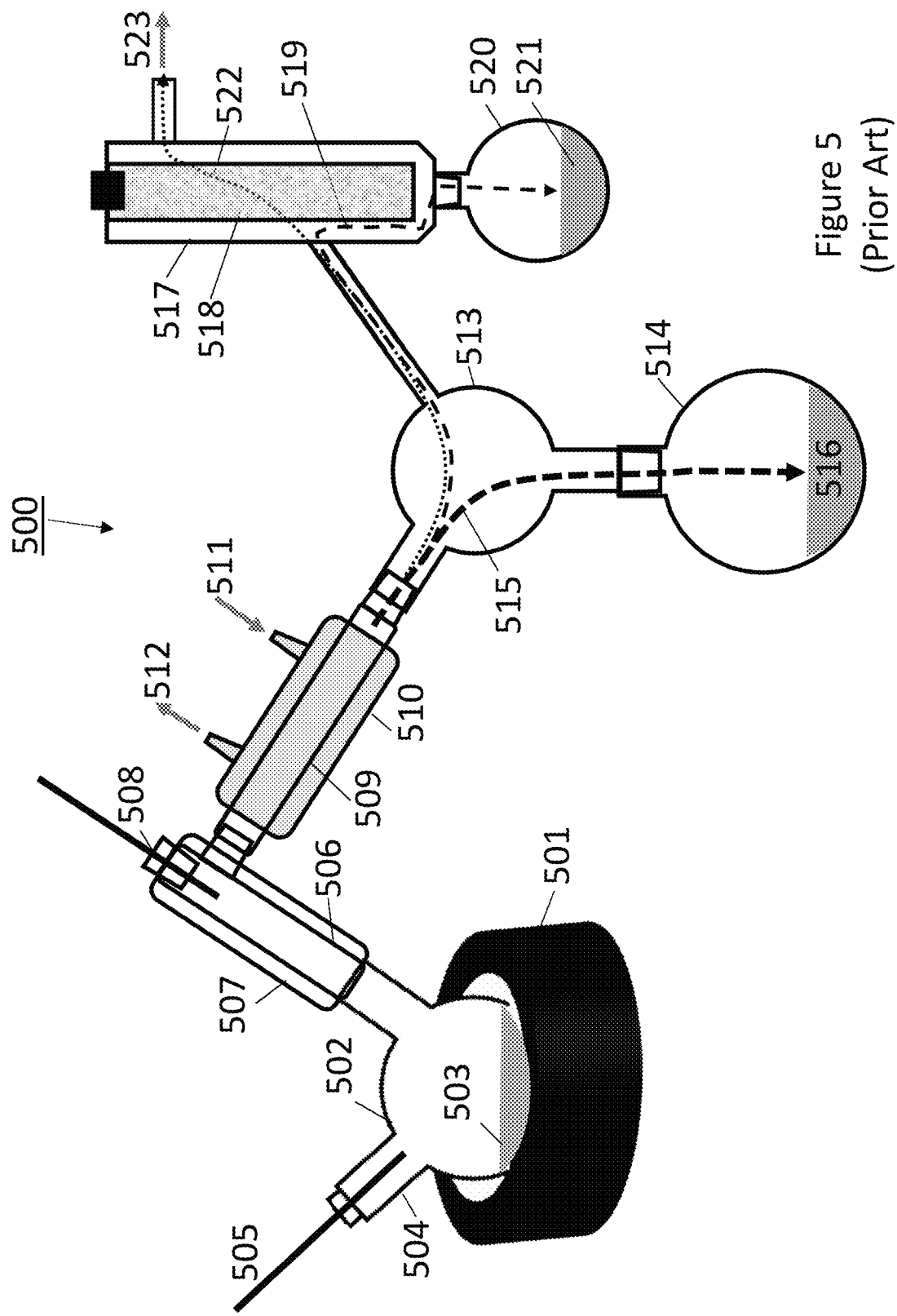
FIG. 5 shows the schematic of a typical short-path distillatory apparatus of the sort used for purification of *cannabis* oil.

FIG. 5 shows the schematic of a typical short-path distiller 500 used for purification of *cannabis* oil. The distiller comprises a distillation material flask 502 associated with a heater 501 to heat the flask contents 503 (e.g., distillation material with the bio-compound) to the required temperature set point. The heater's temperature may be adjusted by computer control and/or manual adjustment on the heater itself. The flask 502 has a port 504 for loading the flask contents 503 as well as for inserting a first temperature sensor 505.

A distillation column 506 having insulated walls 507 is mounted, via a first inlet on the flask 502. The distillation column 506 has a second inlet 508 to accommodate a second temperature sensor 508, and/or additional metrology sensors or other purposes. The distillation column 506 is connected to a Liebig-type or another type of condenser, having a tilted condenser tube 509 surrounded by insulated walls 510, coolant inlet port 511 and a coolant outlet port 512. Connected to the condenser tube 509 is a fraction distribution flask 513 for separating some of the fractions. The flowing distillate 515 travels along a distillation path through the fraction distribution flask 513 and joins a collected distillate 516 which has accumulated in a collection vessel, such as the distillate collection flask 514. Meanwhile, the residual material (primarily comprising undistilled vapors) travels to the cold trap 517. Cold trap 517 has a cooler 518 and is attached to the residual material collection flask 520. The residual material 521 travels along path 519 and accumulates in the residual material collection flask 520. The residual distillation gas 522 present in the cold trap 517 is pumped out from the cold trap 517 through gas port 523.

Figure 6:
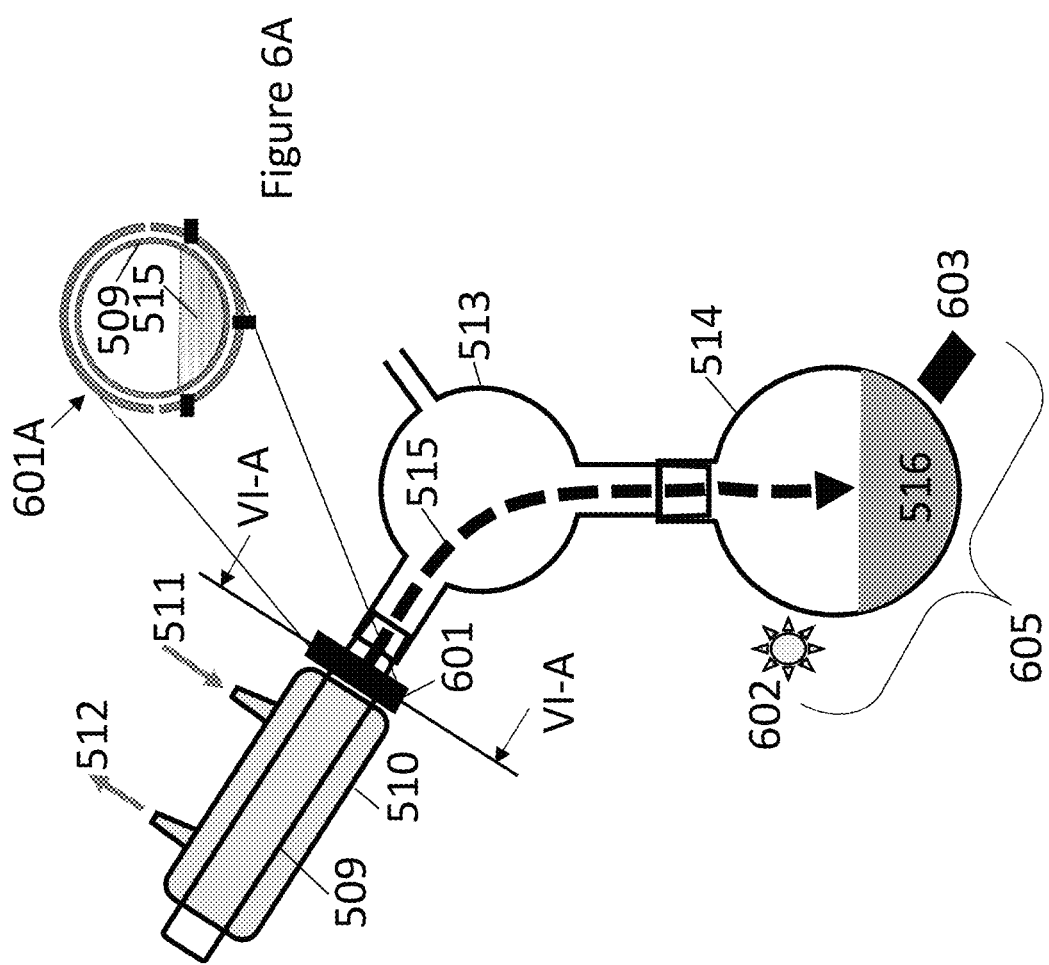
FIG. 6 shows an enlarged view of a portion of the short-path distillatory of FIG. 5, having an in-situ monitoring assembly installed.

FIG. 6 shows a magnified view of the short-path distiller as per FIG. 5, having an in-situ monitoring assembly 601 in accordance with the subjection matter of the present application. The in-situ optical monitoring assembly 601 is removably attached to the condenser tube 509 proximate the latter's exit end, and the optical components of the assembly 601 are arranged to optically monitor the flowing distillate 515 as it is about to exit the condenser tube 509 and enter the fraction distribution flask 513. In some embodiments, the first in-situ optical monitoring assembly 601 includes a fluorometer. In other embodiments, the monitoring assembly 601 can include a spectroscopic device such an absorbance monitor, a polarimeter, a nephelometer/scatterometer or a turbidity meter, or combinations of these.

It is understood that the condenser tube 317 is an optically transparent tube which is configured to permit optical illumination and/or detection through its walls. It is noted, however, that the entire length of the condenser tube 317 need not be optically transparent. Thus, a tube which is painted black along its entire length, except for one or more small regions which are amenable to optical illumination and detection through the walls, would be considered to be an optically transparent tube within the meaning of the present disclosure.

FIG. 6A shows a perpendicular cross-section along lines VIA-VIA, which cross-section is taken proximate the exit end of the condenser tube 509 where the in-situ optical monitoring assembly 601 is located. More particularly, FIG. 6A shows the level of the flowing distillate 515, as it flows in the tilted condenser tube 509, just before it exits the condenser tube and enters the fraction distribution flask 513.

FIG. 6 also shows that an auxiliary optical monitoring assembly 605 is configured to optically monitor the collected distillate 516 which has accumulated in the distillate collection flask 514. The auxiliary optical monitoring assembly 605 may again comprise a shroud or a ribbon-shaped unit encircling the distillate collection flask 514 as described above. The auxiliary optical monitoring assembly 605 can comprise a calibrated white light source 602 illuminating the collected distillate 516, and an optical spectroscopic component 603 optically aligned with the light source 602 and configured to receive the light transmitted through the collected distillate 516. In some embodiments, the auxiliary optical monitoring assembly 605 comprises a colorimeter.

Figure 7:
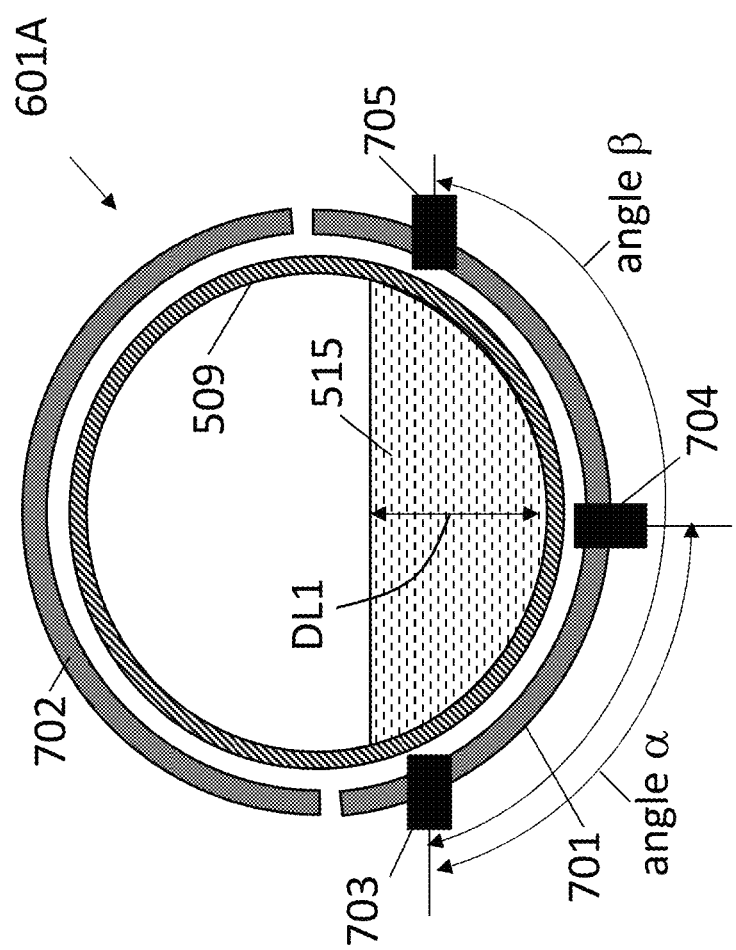
FIG. 7 shows a cross-section of a first arrangement of an in-situ monitoring assembly mounted on a condenser tube.

FIG. 7 shows a detailed view of a first arrangement 601A of the in-situ optical monitoring assembly 601 seen in the cross-section depicted in FIG. 6A. As seen in FIG. 7, the first arrangement 601A comprises a circumferentially extending lower bracket 701 and a complementary circumferentially extending upper bracket 702, together attached to the condenser tube 509 and configured to monitor the flowing distillate 515. As seen in FIG. 7, the brackets 701, 702 each have an inner surface which conforms to a contour of the condenser tube 509, such that the condenser tube 509 is adjacent the corresponding inner surfaces and at least partially nested therein.

The in-situ optical monitoring assembly 601A further comprises a first light source 703 configured to illuminate the flowing distillate 515, a first light detector component 704 circumferentially spaced apart from the first light source 703 by a first angular amount a, and a second light detector component 705 circumferentially spaced apart from the light source 703 by a second angular amount p, the second angular amount being larger than the first angular amount a. The first light detector component 704 is optically aligned to collect a first fluorescing, scattered or polarized component of the light passing through the flowing distillate 515, while the second light detector component 705 is optically aligned to collect the transmitted, scattered or polarized light component of the light passing through the flowing distillate 515.

An optically transparent window, in the form of an aperture ("through hole") or an optical window, may be provided on the conformal inner surfaces of the brackets 701, 702 for each optical component. Each optical component then performs illumination or detection through its associated window.

As seen in FIG. 7, components 703, 704 and 705 are all located adjacent to the tilted condenser tube 509, below the distillate level DL1 of the tilted condenser tube 509, which is typically less than 50% of the diameter of the tilted condenser tube 509. As seen in FIG. 7, all three components 703, 704, 705 are seen to be located within a 180° arc. And so in this first arrangement 601A, all three components 703, 704, 705 can be mounted on just the lower bracket 701 which subtends no more than 180° (i.e., β<180°.

Figure 8:
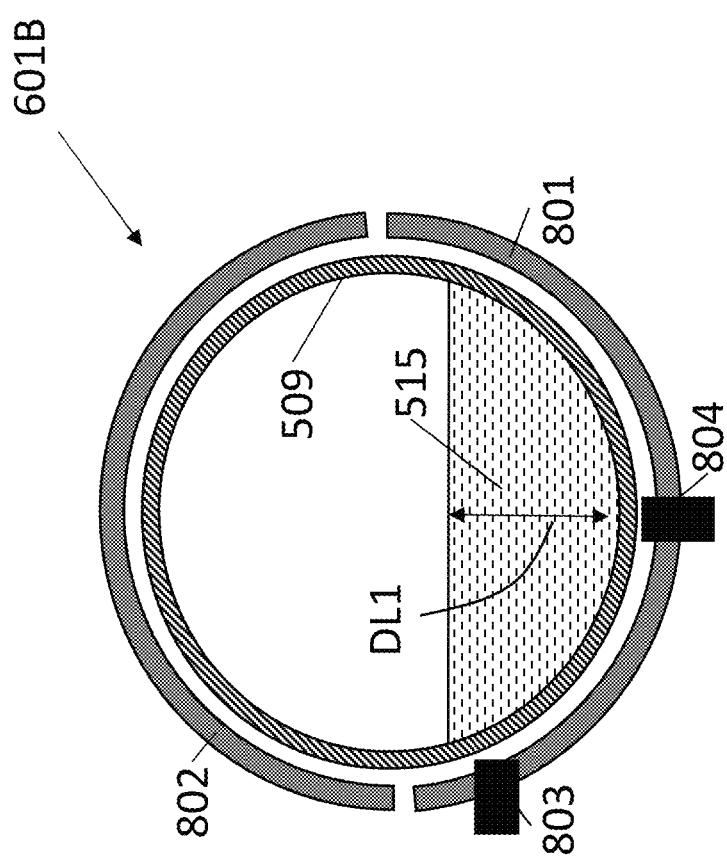
FIG. 8 shows a cross-section of a second arrangement of an in-situ monitoring assembly mounted on a condenser tube.

FIG. 8 shows a cross-section of a second arrangement 601B of the in-situ optical monitoring assembly 601. The second arrangement 601B again includes a circumferentially extending lower bracket 801 and a complementary circumferentially extending upper bracket 802, together attached to the condenser tube 509. The lower bracket 801 carries a light source 803, and a single light detector component 804 optically aligned to collect the fluorescing component of the light passing through the flowing distillate 515.

In some embodiments, the light component 803 emits light at one or more wavelengths chosen from the spectral range 315 nm to 405 nm and the light detector component 804 analyses the fluorescence light collected in the range of 390 nm to 800 nm. In some other embodiments, the light component 803 emits light at one fixed wavelength at 365 nm and the light detector component 804 analyses the fluorescence light collected in the range of 410 nm to 450 nm.

Figure 9:
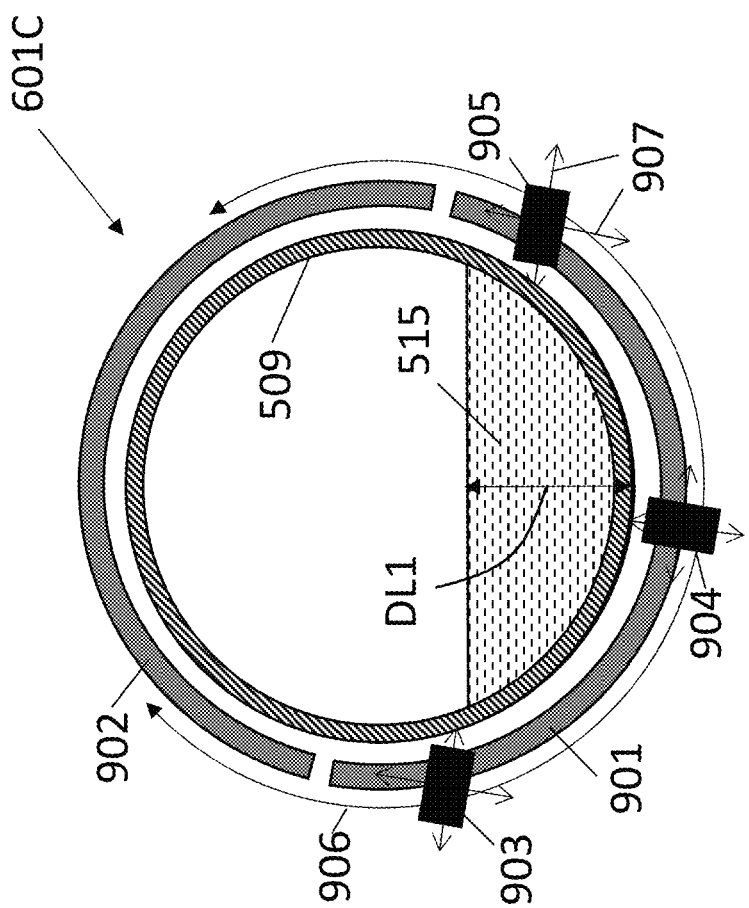
FIG. 9 shows a cross-section of a third arrangement of an in-situ monitoring assembly mounted on a condenser tube.

FIG. 9 shows a cross-section of a third arrangement 601C of the in-situ optical monitoring assembly 601. The third arrangement 601C again includes a circumferentially extending lower bracket 901 and a complementary circumferentially extending upper bracket 902, together attached to the condenser tube 509. The third arrangement 601C comprises a light source 903 illuminating the flowing distillate 515, a first light detector component 904 optically aligned to collect the fluorescing, polarized or scattered component of the light passing through the flowing distillate 515, and a second light detector component 905 optically aligned to collect the transmitted, scattered or polarized light component of the light passing through the flowing distillate 515. However, in the third arrangement 601C, the brackets 901, 902 are configured to be circumferentially rotated together around the periphery of the condenser tube 509. Additionally, the positions of the optical components are adjustable and reconfigurable to facilitate a variety of optical measurements. For instance, the light source 903, and the light detector components 904 and 905 can be adjusted together by rotating the lower bracket 901 to a new angular position indicated by 906. The components 903, 904, 905 may also be individually repositioned relative to one another. For instance, components 903, 904, 905 may individually and independently be moved circumferentially along the lower bracket 901, or even translated and/or tilted along different axes, all as indicated by 907. In sum, in the third arrangement 601C, each of the components 903, 904, 905 is configured and optically aligned in relation to the flowing distillate 515 and its level DL2, separately relative to the monitored liquid as well as relative to each other. This configuration is beneficial for analyzing scattered and polarized light (nephelometry and polarimetry) as well as for optimization of the collected light.

Figure 10:
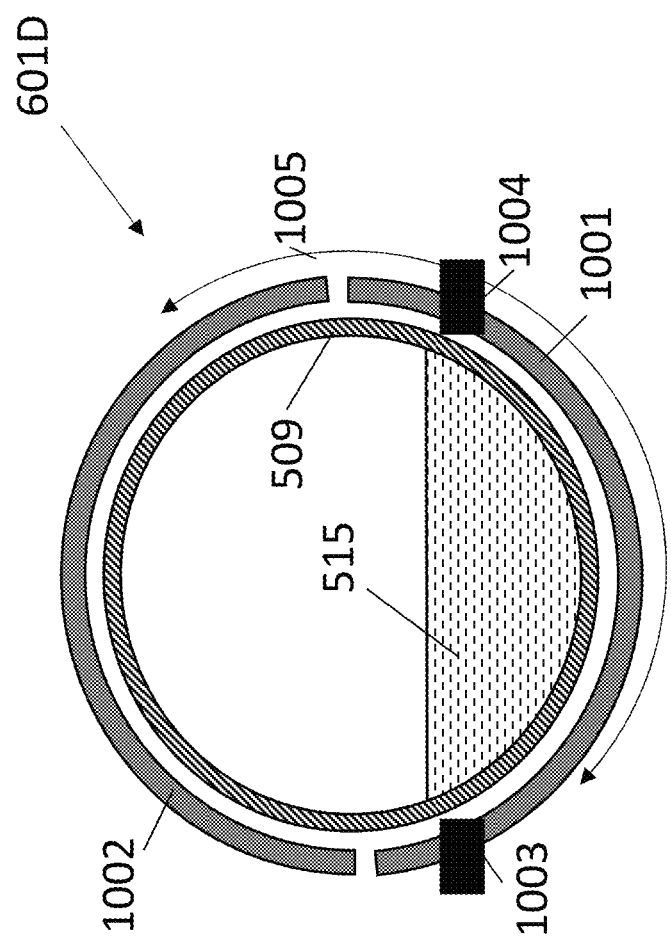
FIG. 10 shows a cross-section of a fourth arrangement of an in-situ monitoring assembly mounted on a condenser tube.

FIG. 10 shows a cross-section of a fourth arrangement 601D of the in-situ optical monitoring assembly 601. The fourth arrangement 601D again includes a circumferentially extending lower bracket 1001 and a complementary circumferentially extending upper bracket 1002, together attached to the condenser tube 509. The lower bracket 1001 carries a light source 1003 and a single light detector component 1004 which is optically aligned to collect the transmitted, scattered or polarized component of the light passing through the flowing distillate 515. The light source 1003 is fixed in relation to the monitored flowing distillate 515, while the light detector component 1004 is reconfigurable along the lower bracket 1001 to detect light at variable angles of incidence, such as by being repositioned to position 1005. To all the light detector components to be repositioned, the lower bracket 1001 may comprise an elongated window associated with each or both of the light detector components. The elongated window is elongated along the circumferential direction of the inner surface. The light detector component(s) may be repositioned at different angular positions along the length of the elongated window so that the light may be detected at variable angles of incidence. The fourth arrangement 601D seen in FIG. 10 may be beneficial for performing polarimetry and nephelometry monitoring as the flowing distillate 515 passes through the condenser tube 509.

Figure 11:
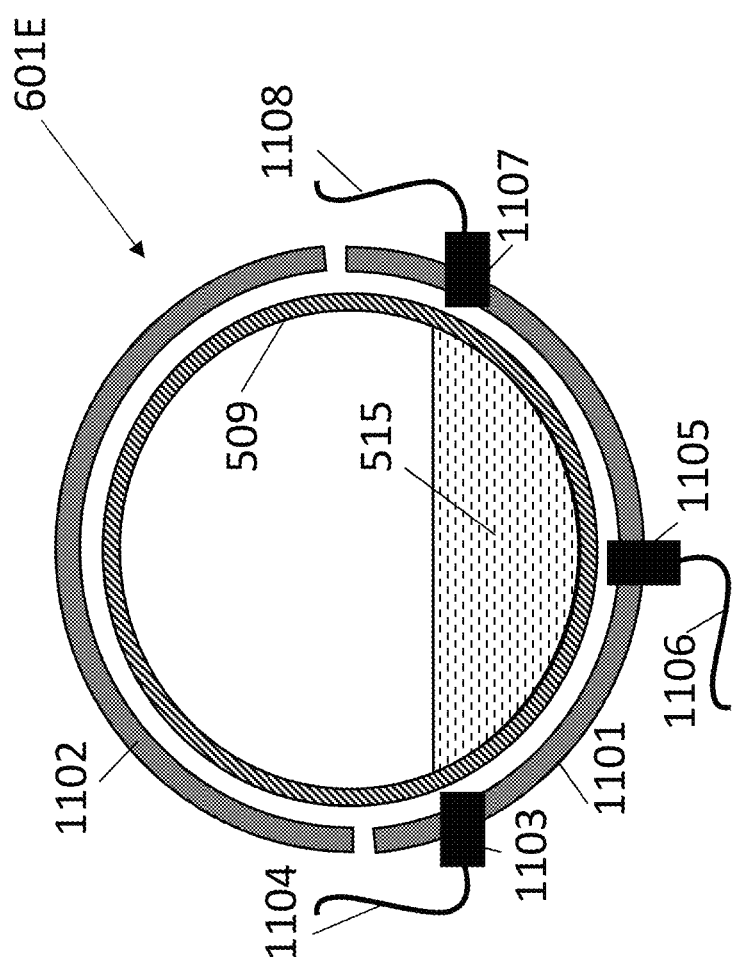
FIG. 11 shows a cross-section of a fifth arrangement of an in-situ monitoring assembly mounted on a condenser tube.

FIG. 11 shows a cross-section of a fifth arrangement 601E of the in-situ optical monitoring assembly 601. The fifth arrangement 601E again includes a circumferentially extending lower bracket 1101 and a complementary circumferentially extending upper bracket 1102, together attached to the condenser tube 509. The lower bracket 1101 comprises a fiber-optics component 1103 with its fiber optic cable 1104, a fiber-optics component 1105 with its fiber optic cable 1106, and a fiber-optics component 1107 with its fiber optic cable 1108. Components 1103, 1105 and 1107 are removably attached to the lower bracket 1101 and are optically aligned to illuminate and collect the light passing through the flowing distillate 515. Components 1103, 1105 and 1107 may be passive optical components such as optical collimators, optical focusers, polarizers and diffusers, but are neither light sources nor light detector components. The optical fibers 1104, 1106 and 1108 guide light between respective optical components 1103, 1105, 1107 and light sources and light detector components remotely located from the windows of optical monitoring assembly, if not remotely located from the optical monitoring assembly itself. Thus, for example, optical fiber 1104 may guide light from a remotely located light source 1111 to passive optical component 1103, while optical fibers 1106, 1108 may guide light from passive optical components 1105, 1107, respectively, to remotely located light detector components 1112, 1113, as seen further below in FIG. 15.

The optical fibers can be single-mode or multi-mode optical fibers. The optical fibers can also be single fibers, double fibers or fiber bundles to serve a variety of optical measurement methods. For example, a double-fiber configuration attached to an optical focuser (e.g., 1103) can have a first fiber guide illuminating light onto the focuser, while the second fiber collects the back-reflected or back-scattered component of the light from the flowing distillate 515.

Figure 12:
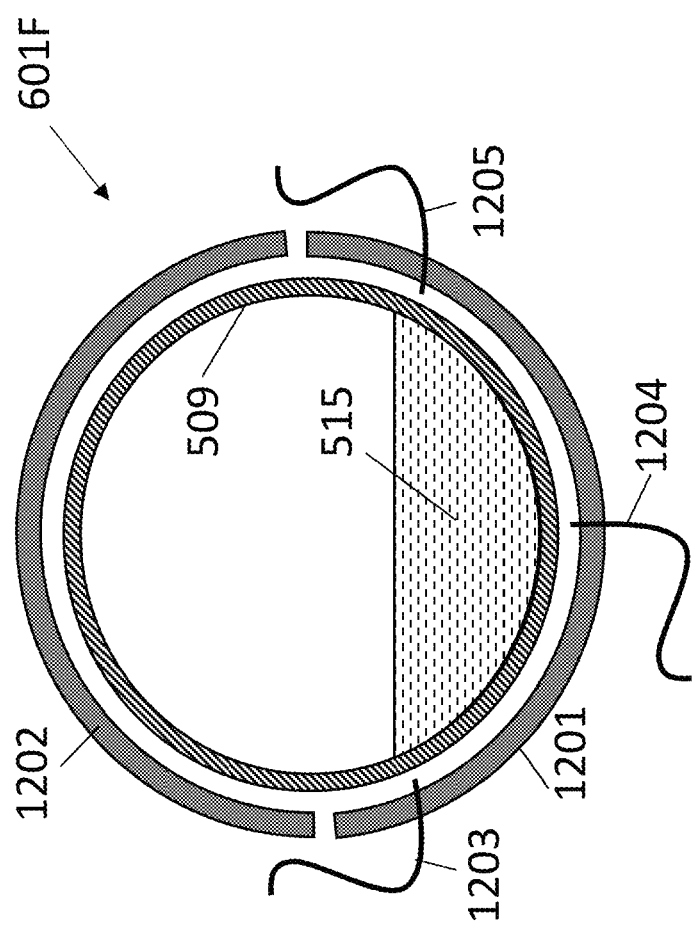
FIG. 12 shows a cross-section of a sixth arrangement of an in-situ monitoring assembly mounted on a condenser tube.

FIG. 12 shows a cross-section of a sixth arrangement 601F of the first optical monitoring assembly. The sixth arrangement 601F again includes a circumferentially extending lower bracket 1201 and a complementary circumferentially extending upper bracket 1202, together attached to the condenser tube 509. The device comprises individual optical fibers or fiber optics cables 1203, 1204 and 1205 which are directly retained by the lower bracket 1202. In this case, no specific fiber optics passive components are provided and the corresponding light beams are guided by the fibers alone. The fiber optics cables each have a first end terminating at a corresponding window and a second end connected to either a remotely located light source or a remotely located light detector. Thus, for example, fiber optics cable 1203 may guide light to the condenser tube 509 from a remotely located light source, while fiber optics cables 1204 and 1205 may guide light from the condenser tube 509 to remotely located light detector components. The optical fibers can be single-mode or multi-mode optical fibers as well as can be single fibers, double fibers or fiber bundles to serve a variety of optical measurement methods. All light sources and light detector components are remotely located away from the monitoring assembly. This configuration is beneficial for low-cost monitoring devices or configurations where the available installation space is very constrained.

In the embodiments of FIGS. 7, 9,11 and 12, one of the three optical components was said to be associated with illumination, and two of three optical components were said to be associated with light detection. However, it is also possible to have two of the optical components associated with illumination, and the remaining optical component associated with light detection. For example in the case of assembly 601A seen in FIG. 7, the third optical component 705 may be a second light source, rather than being a second light detector component. Such an arrangement may be advantageous when it is desired to illuminate the flowing distillate 515 in the condenser tube 509 using two different wavelengths.

Figure 13:
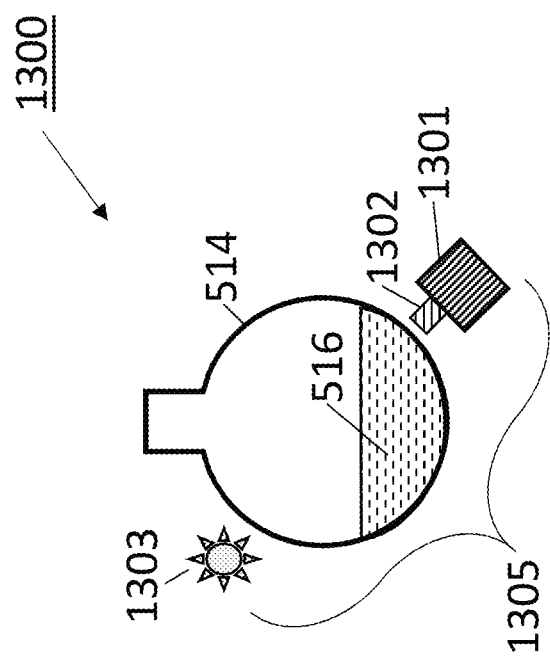
FIG. 13 shows an in-situ monitoring assembly mounted on a collection vessel.

FIG. 13 shows a schematic of one embodiment of the auxiliary optical monitoring assembly 605, which is configured to monitor collected distillate 516 in the distillate collection flask 514. The auxiliary monitoring assembly 605 comprises a spectrometric detector (optical spectrometer) 1301 with an attached cosine corrector component 1302. The spectrometric detector 1301 and the attached cosine corrector component 1302 are of sufficient (small) size to be housed in a shroud or a ribbon-shaped unit which is mounted on, and encircles, the distillate collection flask 514. The light from the calibrated or standard white light source 1303 interacts with the collected distillate 516 and is collected and measured by the spectrometric detector 1301 to retrieve the color coordinates of the distillate 516. Thus, the optical signal received by the spectrometric detector 1301 may be used in conjunction with a colorimeter to gauge the quality of the collected liquid 516.

Figure 14:
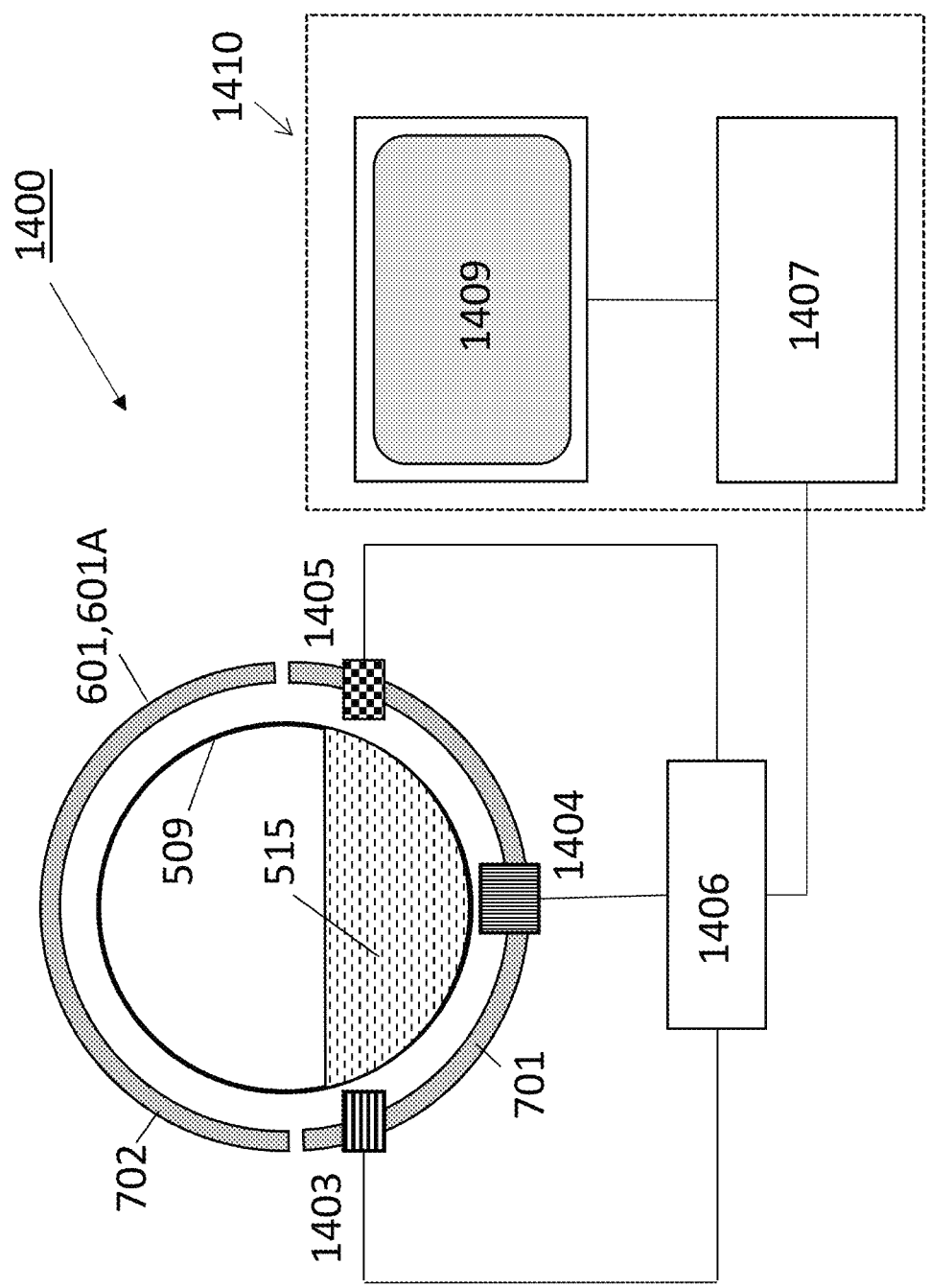
FIG. 14 shows a block diagram of an in-situ optical monitoring system having the first in-situ monitoring assembly of FIG. 7.

FIG. 14 shows a block diagram of an in-situ monitoring system 1400 according to one embodiment of the present invention. System 1400 comprises an in-situ optical monitoring assembly 601 (in this instance, the first arrangement 601A seen in FIG. 7) removably attached to the condenser tube 509. Flowing distillate 515 is seen flowing out of the condenser tube as, also depicted in FIG. 7. In FIG. 14, the in-situ optical monitoring assembly 601A is seen to have lower and upper brackets 701, 702, respectively, just as in FIG. 7. First light source 1403 can be an LED, laser diode, Xe light source or some other illuminating source, which illuminates the flowing distillate 515 in a continuous or pulsed fashion. It may also comprise more than one illuminating component such as more than one LED or any combination of fixed wavelength and broadband optical light sources.

First light detector component 1404 can be a miniature spectrometer, such as Hamamatsu C12880MA (https://www.hamamatsu.com/eu/en/C12880MA.html retrieved Jun. 14, 2018) or NanoLambda NSP32 (https://nano-lambda.myshopify.com/products/nsp32-w, retrieved Jun. 14, 2018) covering the specific wavelength range where the photoluminescence response of the monitored bio-compound is expected. Second light detector component 1405 can be a second miniature spectrometer or an individual photodetector component, configured to collect the transmitted or scattered light from the flowing liquid light beam. Operation of the light components 1403, 1404 and 1405 is controlled by an optical control circuit 1406 comprising a microcontroller such as the 8-bit AtMega 2560 (https://www.microchip.com/wwwproducts/en/ATmega2560 retrieved Jun. 14, 2018). Although two light detector elements 1404, 1405 are shown, it is understood that the system 1400 can also work with only, one of the light detector components.

The system 1400 also includes a computer 1407 and a display 1409, which may be a touch screen display. The touch screen display 1409 may present a process control interface to control an extraction and/or purification system. The display 1409 may also present status information which is updated in real-time, including parametric values, plots, charts and suggestions for actions that can be taken at any given time. In some embodiments, the computer 1407 and the display 1409 are integrated into a single unit 1410. In one embodiment, the computer 1407 and the display 1409 are both provided by a Raspberry Pi Computer Module 3 Lite.

The computer 1407 is also connected to an optical monitoring assembly control circuit 1406 which controls the operation of the in-situ optical monitoring assembly 601, 610A. The computer 1407 hosts all the operation and control software to drive the display 1409 and the control circuit 1406. The drive circuit 1406 may comprise an analog, digital or mixed-signal circuit on a PC board 1601 (See FIG. 16H). In some embodiments, the drive circuit 1406 may be integrated into the in-situ optical monitoring assembly itself, and so the in-situ optical monitoring assembly comprises not only at least one light source 1403 and at least one light detector component 1404, but also may comprise an optical monitoring assembly control circuit 1406.

Figure 15:
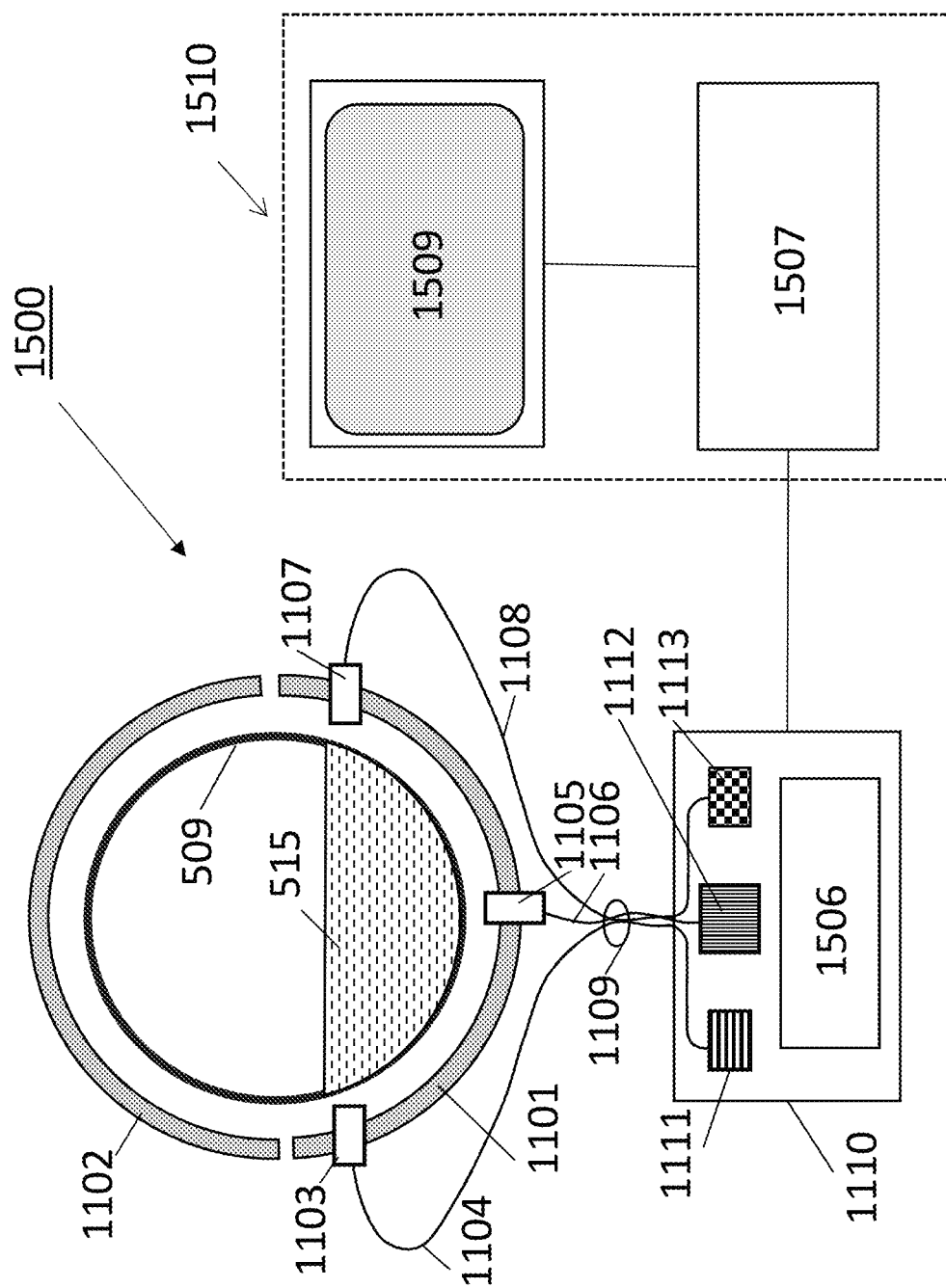
FIG. 15 shows a block diagram of an in-situ optical monitoring system having the first in-situ monitoring assembly of FIG. 11.

FIG. 15 shows a block diagram of an in-situ monitoring system 1500 according to another embodiment of the present invention. In system 1500, optical fibers are used to connect passive light components to light sources and light detector components.

System 1500 comprises an in-situ optical monitoring assembly 601 (in this instance, the fifth arrangement 601E seen in FIG. 11) removably attached to the condenser tube 509. Flowing distillate 515 is seen flowing out of the condenser tube as depicted in FIG. 11. In FIG. 15, the in-situ optical monitoring assembly 601E is seen to have lower and upper brackets 1101, 1102, respectively.

In system 1500, optical fibers 1104, 1106 and 1108 are bundled together into a single fiber optics cable assembly 1109 which is input to an optical control module 1110. Optical control module 1110 contains an optical control circuit 1506 not unlike the optical control circuit 1406 describe with respect to system 1400. In addition to the optical control circuit 1406, the optical control module 1110 may also house a light source 1111 which connects (via fiber optics fiber 1104) to passive light component 1103, and light detector components 1112, 1113 which connect (via fiber optics fibers 1106, 1108, respectively) to passive light components 1105, 1107, respectively. In one embodiment, light detector component 1112 may be a miniature spectrometer of the sort described above, and light detector component 1113 may be another miniature spectrometer or a photodetector. It is understood, however, that in some embodiments, only a single light detector component, such as a miniature spectrometer, may be present.

In a manner analogous to that seen with system 1400, in system 1500, the computer 1507 connects to the optical control module 1110 and the display 1509. And as discussed above with respect to system 1400, the computer 1507 and display may be integrated into a single electronic unit 1510.

In some embodiments, all three of the optical control module 1110 (which includes the optical control circuit 1406 plus the light source and light detector components), the computer 1507 and the display 1510 may be contained in a single unit. In such case, the single unit is connected to the in-situ optical monitoring assembly 601, 601E via the single fiber optics cable assembly 1109. Also in such case, no electrical power need be provided to the brackets 1101, 1102 encircling the condenser tube 509.

FIGS. 16A-16H show an exemplary in-situ optical monitoring assembly 1600 of the sort seen in earlier figures as 601, 601A-601F.

Figure 16A:
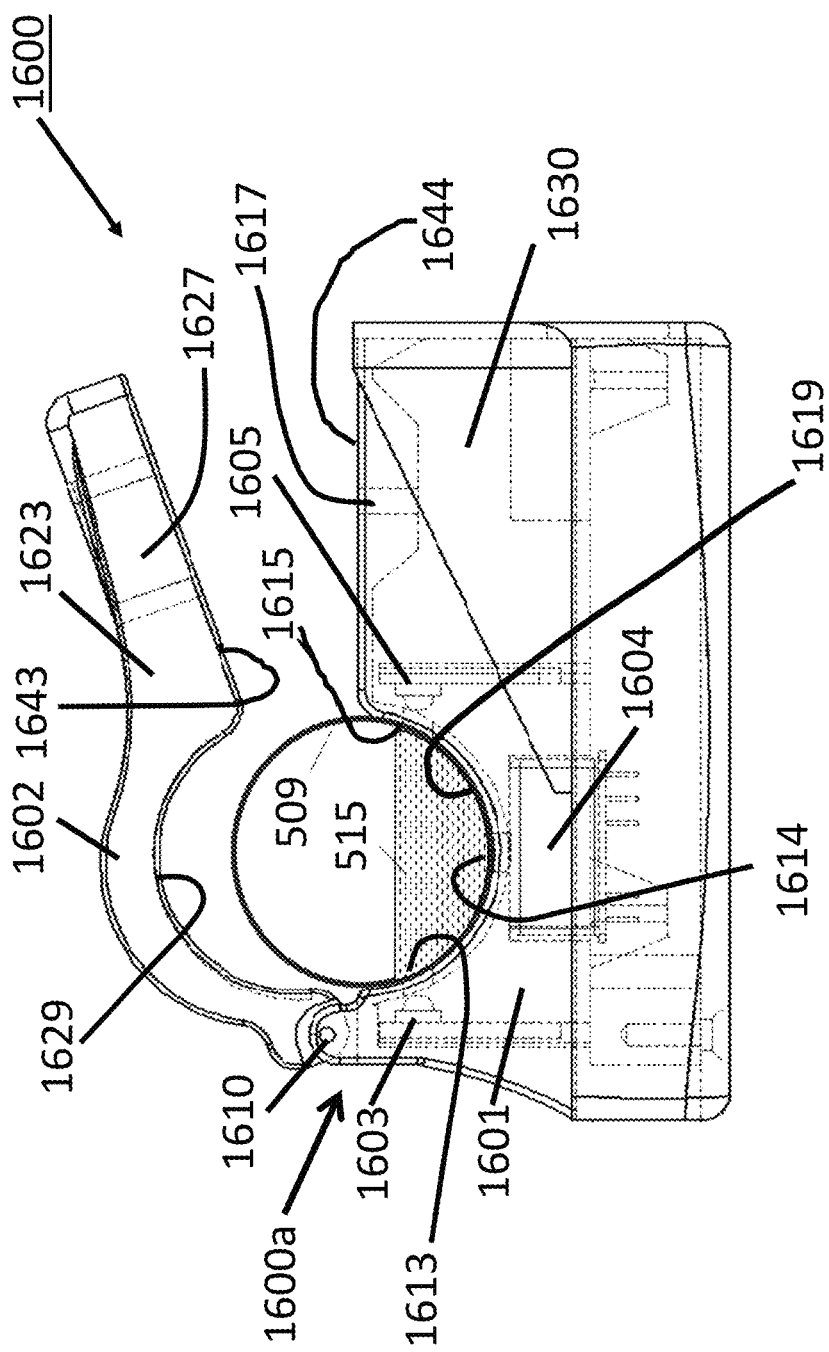
Figure 16C:
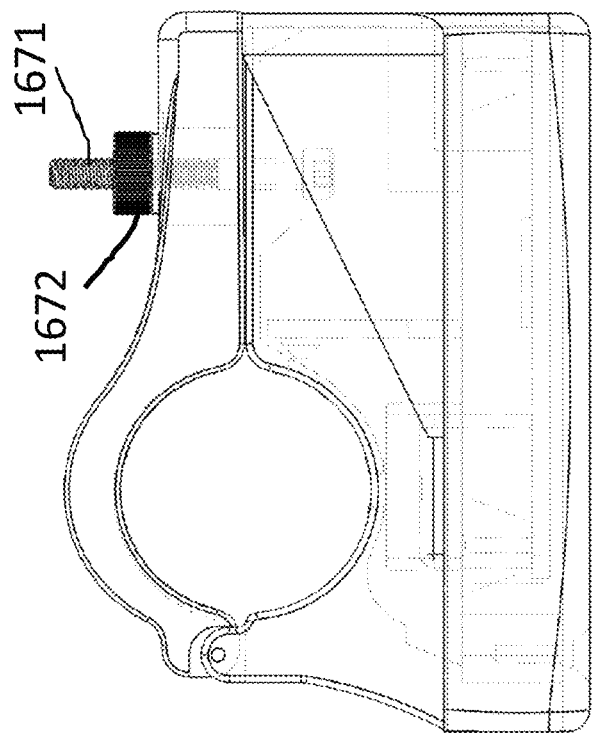
Figure 16B:
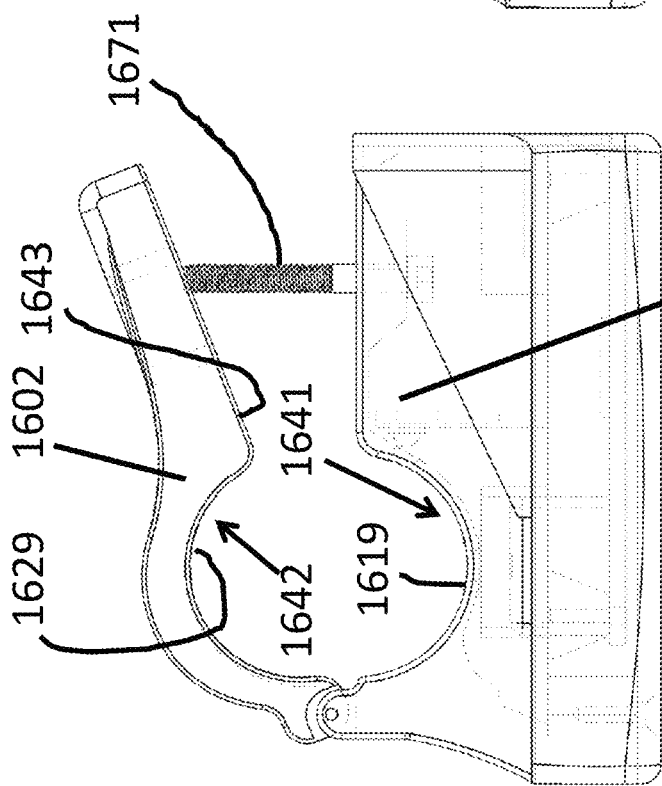
Figure 16E:
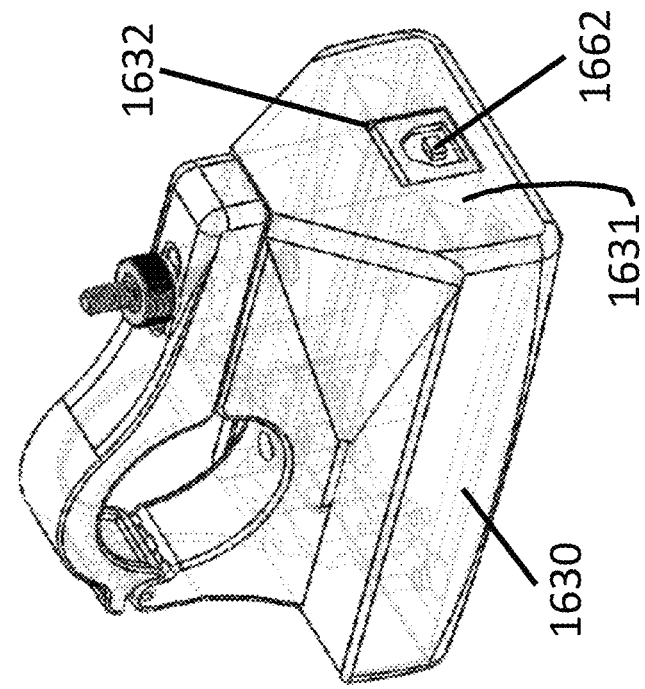
Figure 16D:
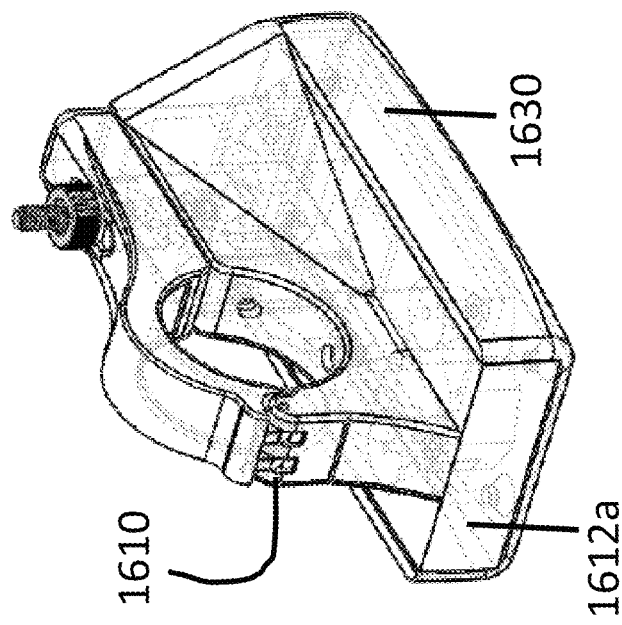

In FIG. 16A, the in-situ optical monitoring assembly 1600 is shown in connection with flowing distillate 515 in a condenser tube 509. It is understood, however, that the in-situ optical monitoring assembly 1600 can also be used in connection with an extract, such as the bio-compounds 110, 318 discussed in conjunction with FIGS. 1-4, which were seen flowing through the siphon exit 109 and the flask inlet 317.

As seen in FIG. 16A, the in-situ optical monitoring assembly 1600 comprises a body 1600a having one or more concave surfaces 1619, 1629 which conform to the contour of opposing surface(s) belonging to the condenser tube 509 through which the liquid flows. The condenser tube 509 seen in FIG. 16A is adjacent the concave surfaces 1619, 1629 and is at least partially nested therein. Ideally, the surfaces 1619, 1629 encircle the condenser tube 509. This helps minimize the ambient light reading the tube's cylinder of fluid, which is covered by the surfaces 1619, 1629.

The body 1600a seen in FIG. 16A comprises a lower bracket 1601 and an upper bracket 1602 hingedly connected to one another by one or more hinges 1610. The lower and upper brackets 1601, 1602 may each comprise a hard plastic resin which may be formed by molding and/or additive manufacture (i.e., "3D printing").

The lower bracket 1601 comprises a housing 1612 configured and dimensioned to accommodate a plurality of optical components 1603, 1604, 1605, shown in phantom. The housing 1612 may include a housing base portion 1612a on top of which is a narrower housing upper portion 1612b (see FIG. 16F). In some embodiments, as seen in FIG. 16H, the lower bracket 1601 can also contain a PC board 1651 to carry the optical monitoring assembly control circuit 1406. The optical components 1603, 1604, 1605, can include a light source 1603 and two light detector components, such as a miniature optical spectrometer 1604 of the sort discussed above, and a photodetector 1605. In some embodiments, however, only the light source 1603 and the miniature optical spectrometer 1604 may be present.

The lower bracket's housing 1612 has a first upper surface portion 1641 comprising a first part-cylindrical concave surface 1619 configured and dimensioned to conform to the contour of one half of a cylindrical condenser tube 509 (or siphon exit 109, flask inlet 317, as appropriate). The first concave surface 1619 may comprise three optically transparent windows 1613, 1614, 1615 which provide a line-of-sight view between respective optical components 1603, 1604, 1605 within the housing 1612 and the flowing distillate 515 (e.g., bio-compound extract) within the condenser tube 509. The optically transparent windows 1613, 1614, 1615 may be in the form of either apertures ("through holes") formed in the first concave surface 1619, or optical windows formed in the first concave surface 1619.

Figure 16G:
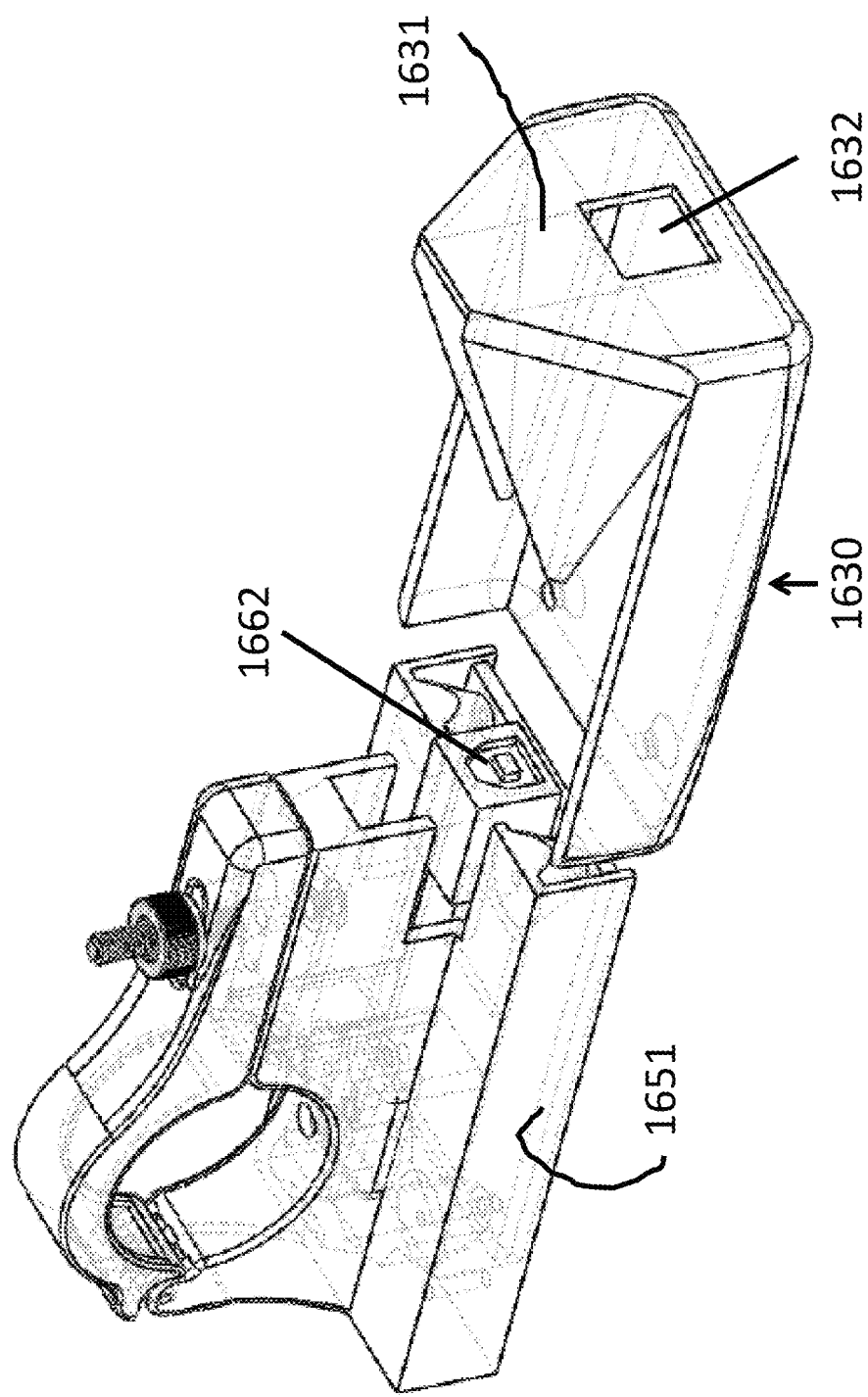

As seen in FIGS. 16F-16H, a base cover 130 may be provided on the housing's base portion 1612a. As seen in the figures, the base cover 1630 may be slidably attached to the housing's base portion 1612a. The base cover 1630 helps protect the housing 1612 and components therein, such as the PC board 1651. The base cover 1630 has, at a central portion of its rear surface 1631, an aperture 1632 to provide access to a connector 1662 formed on a rear surface of the housing 1612. A cable carrying electrical and/or optical signals may thus be connected to the housing's connector 1662 via the base cover's aperture 1632.

The upper bracket 1602 is in the form of a clip, and comprises a handle member 1623 configured to manually adjust the in-situ optical monitoring assembly 1600 between an open state (seen in FIG. 16A) in which the un-situ optical monitoring assembly 1600 can be brought to or removed from, the condenser tube 509, and a closed state (seen in FIGS. 16C-16H) in which the in-situ optical monitoring assembly 1600 is clampingly mounted onto the condenser tube 509. The handle member 1623 of the upper bracket 1602 has a first lower surface portion 1642 comprising a second part-cylindrical concave surface 1629 configured and dimensioned to conform to the contour of the other one half of a cylindrical condenser tube 509. Thus, the first and second concave surfaces 1619, 1629 of the lower and upper brackets complement one another in the sense that they together encircle the condenser tube 509 and constitute a nearly continuous 360° cylindrical surface along a length thereof, when the two brackets 1601, 602 are brought together in a closed state of the assembly 1600.

The handle member 1623 of the upper bracket 1602 also has a second lower surface portion 1643 which, at a location away from the hinge 1610, is provided with a through bore 1627 for accommodating a clamping screw 1671.

The in-situ optical monitoring assembly 1600 has a fastener configured to secure the lower bracket 1601 to the upper bracket 1602 in a closed state of the assembly 1600. In one embodiment, the fastener's complementary components are located on a side of the brackets which is opposite from the hinge 1610. In this regard, lower bracket's housing 1612 has a second upper surface portion 1644 which, at a location away from the hinge 1610, has a first through bore 1617 configured to receive clamping screw 1671 from an underside of the housing's narrow upper portion 1612a. The upper bracket's handle member 1623 has a second lower surface portion 1643 which, at a location away from the hinge 1610, is provided with a second through bore 1627, also configured to receive a clamping screw 1671. As seen from FIGS. 16B-16C, the upper bracket's handle member 1623 may be manually brought over the exposed free end of the clamping screw 1671 so that the latter passes through the second through bore 1627, to bring the lower and upper brackets 1601, 1602 into the closed position. A nut 1672, such as a hex nut (shown), wing nut or the like, may then be used to secure the two brackets around the condenser tube 509.

It is understood that other types of fasteners can be used to secure the two brackets in the closed position. For example, the lower and upper brackets may be provided with detents, springs, catches, etc. to form a lock, a snap-fit, a friction-fit, or the like, when the in-situ optical monitoring assembly 1600 is brought to capture a condenser tube 509 and the lower and upper brackets 1601, 1602 are brought together into the closed state to be secured.

In the above description, the in-situ optical monitoring assembly 1600 is seen to have a body 1600a comprising two brackets. However, in other embodiments, the body may comprise a different number of brackets.

In one embodiment, the body comprises a single bracket having a radially inner arcuate surface subtending more than 180° and less than 210°. In a first variation, the tube-facing portion of the single bracket has a C-shaped cross-section. The bracket comprises a resilient material and is configured to expand in the outward radial direction when pressed against the condenser tube, resulting in the arcuate inner surface also expanding and allowing the bracket to snap onto the condenser tube. Alternatively, the bracket may be mounted over an end of the condenser tube and slid into position. In a second variation, the single bracket is ring-shaped and subtends 360°. In this instance, the bracket is mounted over an end of the condenser tube and slid into position.

In another embodiment, the body comprises three or more brackets linked to one another (e.g., by hinges). Again, the brackets which accommodate optical component(s) have concave surface portions which conform to a contour of the condenser tube, with the windows being formed in those conformal concave surface portions.

Figure 17:
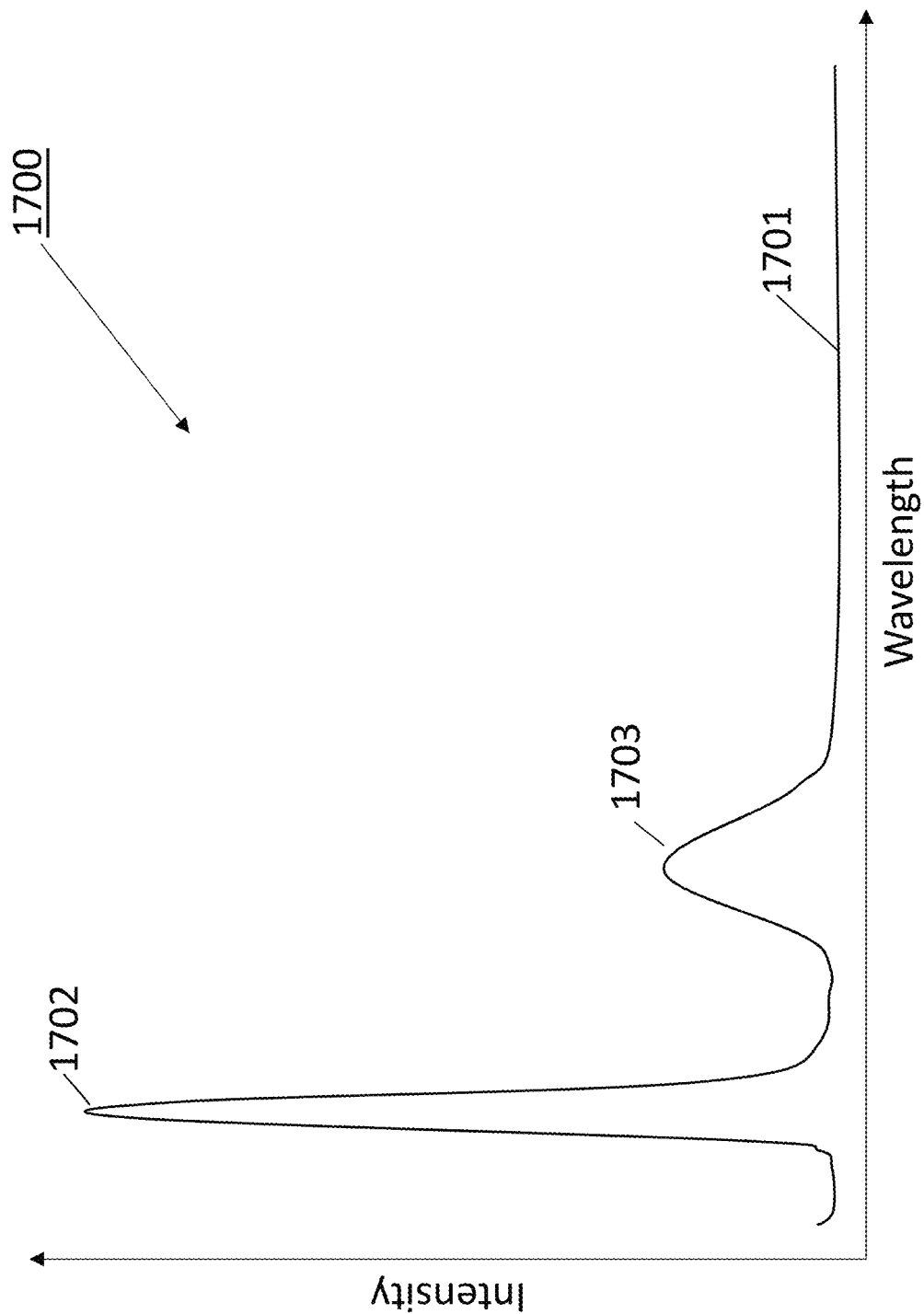
FIG. 17 shows an exemplary broadband photoluminescence spectrum.

FIG. 17 shows an example of optical spectrum 1700 collected by the miniature optical spectrometer 1404 during operation of the in-situ monitoring system 1400 shown in FIG. 14. The spectral curve 1701 has two distinguished features, related to the distillation process. Peak 1702 is associated with the illuminating light from light source 1403, which, although propagating perpendicularly to miniature spectrometer 1404, still might be able to partially couple into the spectrometer 1404. Peak 1703 is associated with the optical response of the flowing distillate 515. Peaks 1702 and 1703 are closely correlated to each other. The illuminating light from light source 1603 excites the bio-compound in the flowing distillate 515, causing it to photoluminescence at the longer wavelength of the spectrum.

By monitoring over time, the spectral wavelengths, the areas under the peaks, peak heights, etc., one can (a) determine when species of interest are present in newly-formed flowing distillate 515 within the condenser tube 509, and collect flowing distillate 515 in the distillate collection flask 514 only when such species of interest are present in sufficient concentrations. The monitoring can be done visually by an operator. In a more automated mode, upon detection of a predetermined condition, an alarm or signal is issued. In some embodiments, the alarm or signal may be sent to an operator's laptop smart phone, computer of other communication device, such as by SMS-text In one specific use of the in-situ monitoring system 1400, the illuminating light from component 1603 contains one or more discrete wavelengths in the range 315-405 nm, while the photoluminescence response of the cannabinoid bio-compound in the flowing liquid 515 is in the range 405-800 nm.

Figure 18:
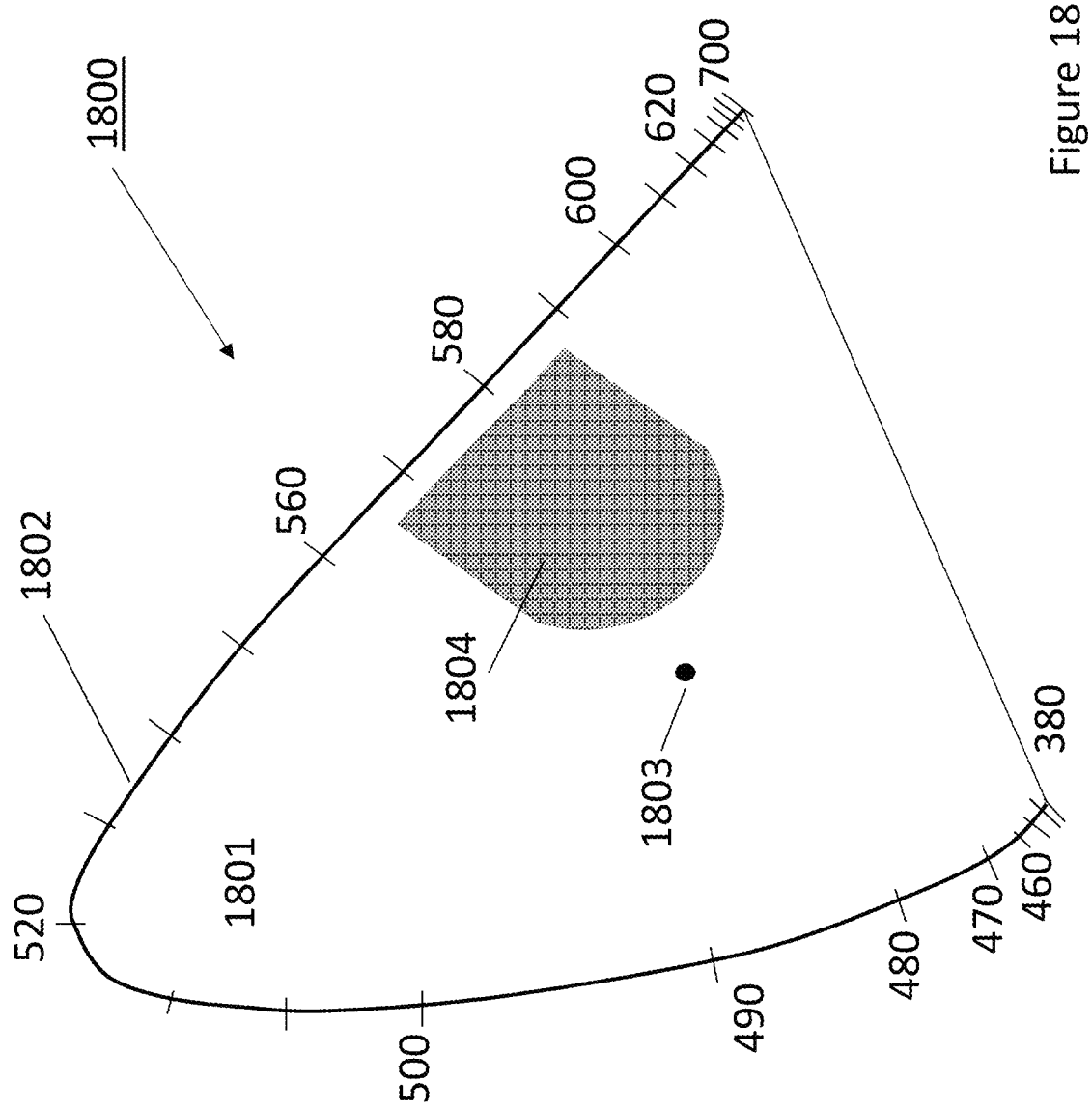
FIG. 18 shows an exemplary CIE L*a*b plot with the color coordinate area associated to an extracted bio-compound.

FIG. 18 shows a typical CIE L*a*b* color space 1800, which may be displayed when using the second in-situ optical monitoring assembly 405, 605 (see FIGS. 4 & 6) to determine optical properties of the collected liquids 318, 516 in the distillate collection flask 316, 514. The CIE L*a*b* space is shown in position 1801. All natural colors can be identified by their positional coordinates in the CIE L*a*b* space. The corresponding spectral wavelengths, bordering the color space, are shown by the curve 1802. The most saturated natural colors are located closer to curved border line 1802, while less saturated colors are positioned away from the border line 1802 and closer to the center of the space, with the white color being in the very center of the space—position 1803. As an example, color coordinates in a first region 1804 of the color space may correspond to collected liquid 318, 516 that is deemed acceptable, while color coordinates outside the first region 1804 may correspond to collected distillate 318, 516 that is deemed unacceptable. Thus, an operator viewing a display showing the color space may be able to quickly determine, based on colorimetry, whether the collected liquid 318, 516 in a given distillate collection flask 316, 514 should be accepted or rejected. Furthermore, a comparison of the color coordinates of collected liquid 318, 516 with the color coordinates of a standard high-quality and high purity reference distillatory liquid, can be used to determine the dilution and the purity of the collected distillate 318, 516.

Figure 19:
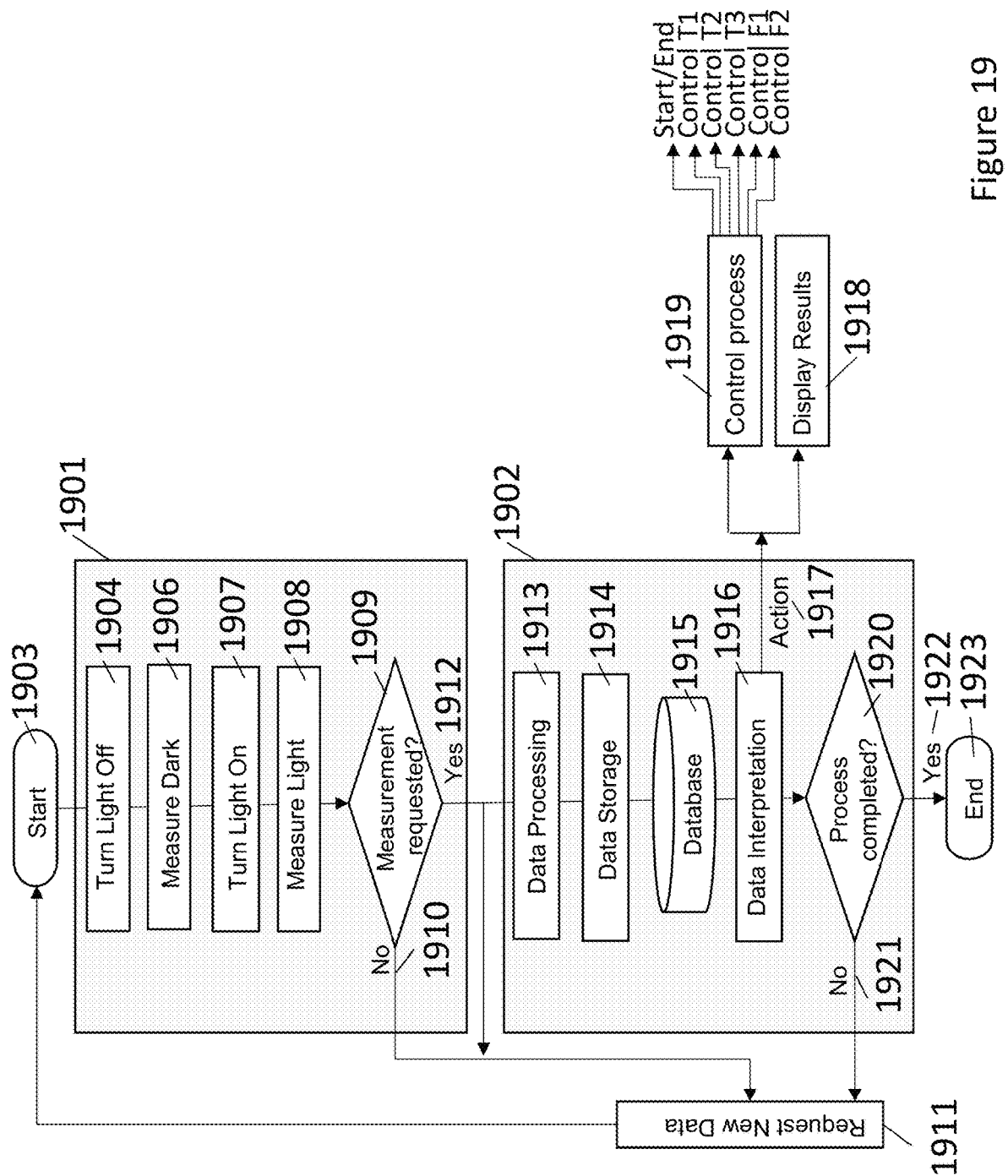
FIG. 19 shows the block scheme of the operation software of an in-situ optical monitoring system in accordance with one embodiment of the present invention.

FIG. 19 shows a block-scheme of the software operation for the in-situ optical monitoring system 1400 seen in FIG. 14. FIG. 19 presents two separately identifiable blocks: block 1901 shows the operations associated with the in-situ optical monitoring assembly 601, controlled by control circuit 1406, while block 1902 shows the operations of the control software program module residing in the computer 1407. Block 1901 is constantly looping when system 1400 is turned on, while block 1902 requests measurement data produced by the operation of block 1901 only when the control software module in computer 1407 determines the need for it.

The operation of block 1901 is performed on cycles, which repeat continuously. The cycle starts at step 1903 and a dark spectrum reference (i.e., the detected spectrum in the absence of illumination) is taken. At step 1904, the controller 1406 turns off the light source 1403. Next, at step 1906, the detector components 1404 and 1405 measure the dark spectrum reference.

Next, at step 1907, the light at component 1403 is turned on and at step 1908, the components 1404 and 1405 measure the light. Once this cycle is done, the system reaches a decision point at step 1909, in which the controller 1406 determines whether not a measurement has been requested by the control software program in computer 1407. If it is determined at step 1909 that a measurement has not been requested 1910, no measurement is provided to the computer 1407 and the loop of operation block 1901 continues at step 1911. If, on the other hand, it is determined at step 1909 that a measurement has been requested 1912, the measurement data is sent on to the computer 1407, and again the loop of operation block 1901 continues at step 1911.

When the measurement data is sent on to the control software module in computer 1407 pursuant to a request, the steps in block 1902 are invoked.

First, in step 1913, the measurement data undergoes various processing steps to condition the data, such as by filtering, moving average calculations and regression. Then, in step 1914, the processed measurement data is stored in memory and in step 1915 organized into a database.

In step 1916, information taken from the database, such as historic measurements, response models, statistical and phenomenological models, is compared with the most recent measurement data to interpret the measurement data. During the interpretation process various process decisions are made by the software such as identifying bio-components, detecting the presence of contaminants, purity, potency, among others.

In response to these interpretations, in step 1917, the computer control module may display information to an operator, issue an alarm or signals, and/or issue actionable commands, as seen in steps 1918 and 1919.

In step 1918, the computer control module may display results in the form of optical spectra 1700, color space charts 1800, status and other information pertaining to the flowing distillate 515 and/or the collected distillate 516. The displayed information may include the aforementioned absorbance, turbidity, scattering, photoluminescence, nephelometric and polarimetric parameters, which are updated in real-time, since the illumination and detection proceeds continuously.

Suggestions for changing the extraction/purification process conditions, such as temperatures, pressures, volumetric flow rates, etc. may also be displayed. For instance, one action may be to adjust the temperature of the heater 501 used in the distillation process (FIG. 5). Another action may be to initiate and/or discontinue collecting distillate in the distillate collection flask 514 (FIG. 13), depending on information obtained from the optical signal received at the light detector(s). In step 1919, an operator can take appropriate action to control the process, via the touch-screen display 1409 and/or other user input devices associated with the computer 1407. In a web-enabled environment, communication of information and commands may be done with a smart phone or other platform in the hands of a remote operator.

In step 1920, the computer control module determines whether the entire extraction or purification process has completed. If it is determined that the process has not completed 1921, the loop of operation block 1901 continues at step 1911 and new data is requested. If, on the other hand, it is determined that the entire process has completed 1922, the process is terminated 1923 so that no additional measurements are taken, appropriate alarms, signals and information is sent, and the entire system is turned off.

And as explained above, absorbance, turbidity, scattering, photoluminescence, nephelometric and polarimetric parameters, among others, may be obtained. And since the illumination and detection proceeds continuously, the various parameters may be updated in real time on the display screen 1409, 1509.

What is claimed is:

1. An in-situ optical monitoring assembly configured to fit onto an optically transparent tube having liquid passing therethrough, the in-situ optical monitoring assembly comprising:
  a body having one or more surfaces which conform to a contour of an optically transparent tube;
  first and second optically transparent windows formed in the one or more surfaces; and
  first and second optical components mounted within the body and positioned at the first and second windows, respectively, such that a direct line of sight is provided between each of the first and second optical components and an exterior of the body, through respective first and second windows; wherein:
  the first optical component is a light source positioned at the first window; and
  the second optical component is a first light detector component positioned at the second window, the first light detector component comprising an optical spectrometer.

2. The in-situ optical monitoring assembly according to claim 1, wherein:
the body comprises a single bracket comprising a resilient material having a radially inner arcuate surface subtending more than 180° and less than 210°;
the windows are formed on the inner surface at spaced apart locations along the arcuate inner surface; and
the bracket is configured to expand in the outward radial direction when pressed against an optically transparent tube, resulting in the arcuate inner surface also expanding and allowing the bracket to snap onto the optically transparent tube.

3. The in-situ optical monitoring assembly according to claim 1, wherein:
the body comprises a single bracket having a radially inner arcuate surface subtending 360°;
the windows are formed on the inner surface at spaced apart locations along the arcuate inner surface;
the bracket is configured to be mounted over an end of an optically transparent tube.

4. The in-situ optical monitoring assembly according to claim 1, wherein:
the body comprises three or more brackets connected to one another.

5. The in-situ optical monitoring assembly according to claim 1, wherein:
the body comprises:
a first bracket having a first concave surface which conforms to a contour of an optically transparent tube; and
a second bracket having a second concave surface which conforms to a contour of an optically transparent tube; and
the assembly is adjustable between:
an open state in which the first and second concave surfaces do not face each other; and
a closed state in which the first and second concave surfaces face each other.

6. The in-situ optical monitoring assembly according to claim 5, further comprising:
a hinge connecting a first end of the first bracket to a first end of the second bracket; and
a fastener configured to secure the first bracket to the second bracket in the closed state of the assembly, the fastener being located on a side of the brackets which is opposite from the hinge.

7. The in-situ optical monitoring assembly according to claim 5, wherein:
each of the first and second concave surfaces subtends an angle of about 180°; and
in a closed state of the assembly, the first and second concave surfaces together form a nearly continuous 360° cylindrical surface.

8. The in-situ optical monitoring assembly according to claim 5, wherein:
the first and second windows are both formed in the first concave surface, and are circumferentially spaced apart from one another by a first angular distance.

9. The in-situ optical monitoring assembly according to claim 8, wherein:
the second window is elongated in a circumferential direction of the first concave surface; and
the first light detector component is configured to be repositioned along a length of the first concave surface so that light may be detected at variable angles of incidence through the elongated window.

10. The in-situ optical monitoring assembly according to claim 8, further comprising:
a third window formed in the first concave surface and circumferentially spaced apart from the first window by a second angular distance which is larger than the first angular distance; and
a third optical component mounted within the body and positioned at the third window; wherein:
the third optical component is a second light detector component positioned at the third window.

11. The in-situ optical monitoring assembly according to claim 8, further comprising:
a third window formed in the first concave surface and circumferentially spaced apart from the first window by a second angular distance which is larger than the first angular distance; and
a third optical component mounted within the body and positioned at the third window; wherein:
the third optical component is a second light source positioned at the third window.

12. The in-situ optical monitoring assembly according to claim 11, wherein:
the first light source and the second light source are configured to emit light at different wavelengths.

13. The in-situ optical monitoring assembly according to claim 8, wherein:
the first bracket houses the light source, the first light detector component, and an optical control circuit configured to control operation of the light source and the first light detector component.

14. The in-situ optical monitoring assembly according to claim 13, wherein:
the first bracket also houses a second light source.

15. The in-situ optical monitoring assembly according to claim 13, further comprising a connector provided on a surface of the first bracket.

16. The in-situ optical monitoring assembly according to claim 13, wherein the first bracket further comprises:
a housing having a housing base portion on top of which is a narrower housing upper portion; and
a base cover slidably mounted to the housing base.

17. The in-situ optical monitoring assembly according to claim 8, wherein:
the first bracket houses the light source and the first light detector component; and
the second bracket is devoid of light sources and light brackets.

18. The in-situ optical monitoring assembly according to claim 17, wherein:
the first angular distance is less than 180°.

19. The in-situ optical monitoring assembly according to claim 17 wherein:
the first bracket also houses a second light detector component.

20. The in-situ optical monitoring assembly according to claim 17 wherein:
the first bracket also houses a second light source.

21. An in-situ optical monitoring system configured to monitor a liquid flowing in an optically transparent tube, the system comprising:
an in-situ optical monitoring assembly configured to fit onto an optically transparent tube having liquid passing therethrough, the in-situ optical monitoring assembly comprising:
a body having one or more surfaces which conform to a contour of an optically transparent tube;

first and second optically transparent windows formed in the one or more surfaces; and first and second optical components mounted within the body and positioned at the first and second windows, respectively, such that direct line of sight is provided between each of the first and second optical components and an exterior of the body, through respective first and second windows; wherein:

the first optical component is a light source positioned at the first window;

the second optical component is an optical spectrometer positioned at the second window;

an optical control circuit configured to control operation of at least one of the optical components; and a computer and display integrated into a single unit, the computer configured to control the optical control circuit; wherein:

the optically transparent tube comprises a tilted condenser tube provided with insulated walls, a coolant inlet port and a coolant outlet port; and the in-situ optical monitoring assembly is removably attached to the condenser tube proximate an exit end of the condenser tube such that the optical components of the in-situ optical monitoring assembly are arranged to optically monitor the flowing liquid prior to the liquid exiting the condenser tube.

22. The in-situ optical monitoring system according to claim 21, wherein: the light source, the optical spectrometer and the optical control circuit are all integrated into the in-situ optical monitoring assembly.

23. The in-situ optical monitoring system according to claim 21, wherein: the optical control circuit is integrated into the single unit, along with the computer and the display; and the single unit is connected to the in-situ optical monitoring assembly via fiber optics cables.

24. The in-situ optical monitoring system according to claim 21, wherein:

the display is a touch screen display configured to provide a process control interface to monitor and control an extraction and/or purification process.

25. The in-situ optical monitoring system according to claim 21, wherein:

the first and second windows are circumferentially spaced apart from one another by a first angular distance of less than 180°.

26. An in-situ method of optically monitoring and/or controlling extraction or purification of a liquid obtained from plant material while the liquid flows in an optically transparent tube towards a collection vessel in which the liquid is collected, the method comprising:

providing in-situ optical monitoring assembly comprising:

a body having one or more surfaces which conform to a contour of an optically transparent tube;

first and second optically transparent windows formed in the one or more surfaces; and first and second optical components mounted within the body and positioned at the first and second windows, respectively, such that direct line of sight is provided between each of the first and second optical components and an exterior of the body, through respective first and second windows;

wherein:

the first optical component is a light source positioned at the first window; and the second optical component is an optical spectrometer positioned at the second window;

mounting the in-situ optical monitoring assembly onto the optically transparent tube such that:

the optically transparent tube is at least partially nested in said one or more surfaces which conform to the contour of the optically transparent tube; and the light source and the optical spectrometer are in direct view of the flowing liquid;

illuminating, via the light source, the flowing liquid; and detecting, via the optical spectrometer, a first optical signal resulting from illuminating the flowing liquid.

27. The in-situ method of claim 26, wherein the optically transparent tube is tilted so that the liquid flows due to the effect of gravity.

28. The in-situ method of claim 26, wherein:

said one or more surfaces which conform to the contour of the optically transparent tube are concave and encircle a length of the optical transparent tube.

29. The in-situ method of claim 26, further comprising:

in response to the first optical signal, issuing an alarm to an operator of equipment used in the extraction and/or purification.

30. The in-situ method of claim 26, wherein the method further comprises:

based on the first optical signal, sending spectral information from the in-situ monitoring assembly to a computer; and in response to information in the spectral information, determining at least one action to be taken to affect the extraction or purification process.

31. The in-situ method of claim 26, wherein:

the in-situ optical monitoring assembly further comprises:

a third optically transparent window formed in the one or more surfaces; and a third optical component mounted within the body and positioned at the third windows such that direct line of sight is provided between the third optical component the flowing liquid, through the third window; wherein:

the third component is a light detector; and the method further comprises:

receiving a second optical signal at the third optical component.

32. The in-situ method of claim 26, wherein:

the first and second windows are circumferentially spaced apart from one another by a first angular distance of less than 180°.

33. The in-situ method of claim 26, further comprising: in response to detecting the first optical signal, sending spectral information from the in-situ monitoring assembly to a computer;

analyzing the spectral information; and in response to analyzing the spectral information, determining at least one action to be taken to affect the extraction or purification process.

34. The in-situ method of claim 33, further comprising:

Illuminating collected liquid which had accumulated in the collection vessel and detecting light from the collected liquid;

obtaining spectral information from the light detected from the collected liquid; and based on the spectral information, determining a quality of the collected liquid.

35. The in-situ method of claim 26, wherein:
the plant material is *cannabis*; and
the flowing liquid contains a cannabinoid bio-compound; and
the method comprises:
illuminating the cannabinoid bio-compound at one or more wavelengths in the range of 315 to 405 nm; and
detecting a photoluminescence response of the cannabinoid bio-compound in the flowing liquid in the range 405 to 800 nm.

36. The in-situ method of claim 35, comprising:
illuminating the cannabinoid bio-compound at a wavelength of 365 nm; and
analyzing fluorescent light collected in the range of 410 nm to 450 nm.

37. The in-situ method of claim 26, further comprising:
in response to the first optical signal, determining at least one action to be taken to affect the extraction or purification process.

38. The in-situ method of claim 37, wherein:
the at least one action to be taken comprises discontinuing collection of the liquid in the collection vessel.

39. The in-situ method of claim 37, comprising:
in response to the first optical signal, changing a temperature of a heating element configured to heat solvent during extraction of the liquid from the plant material.

40. The in-situ method of claim 26, further comprising: in response to detecting the first optical signal, sending
spectral information from the in-situ monitoring assembly to a computer;
analyzing the spectral information to determine one or more of absorbance, turbidity, scattering, photoluminescence, nephelometric and polarimetric parameters, of the flowing liquid; and
in response to analyzing the spectral information, determining at least one action to be taken to affect the extraction or purification process.

41. The in-situ method of claim 40, wherein:
the at least one action to be taken comprises discontinuing collection of the liquid in the collection vessel.

42. The in-situ method of claim 41, wherein:
the plant material is *cannabis;*
the flowing liquid contains a cannabinoid bio-compound; and
the at least one action to be taken comprises discontinuing collection of the extracted or purified cannabinoid bio-compound in the collection vessel.

43. The in-situ method of claim 40, comprising:
Illuminating collected liquid which had accumulated in the collection vessel and detecting transmitted light which has passed through the collected liquid;
obtaining colorimetric information from the transmitted light; and
based on the colorimetric information, determining a quality of the collected liquid.

44. An in-situ method of optically monitoring and/or controlling extraction or purification of a liquid obtained from plant material while the liquid flows in an optically transparent tube towards a liquid collection vessel in which the liquid is collected, the method comprising:
mounting onto the optically transparent tube, a device comprising at least first and second optical components and one or more surfaces which conform to the contour of the optically transparent tube, such that:
the optically transparent tube is at least partially nested in said one or more surfaces of the device, and
the first and second optical components are in direct view of the flowing liquid;
illuminating, via the first optical component, the flowing liquid;
detecting, via the second optical component, an optical signal resulting from illuminating the flowing liquid with the first optical component;
performing spectroscopic analysis of the optical signal to determine one or more of absorbance, turbidity, scattering, photoluminescence, nephelometric and polarimetric parameters, of the flowing liquid; and
in response to said spectroscopic analysis, determining at least one action to be taken to affect the extraction or purification process, while the extraction and purification process continues;
wherein: the first optical component is a light source; and the second optical component is an optical spectrometer.

45. The in-situ method of claim 44, wherein the optically transparent tube is tilted so that the liquid flows due to the effect of gravity.

46. An in-situ optical monitoring system configured to monitor a liquid flowing in an optically transparent tube, the system comprising:
an in-situ optical monitoring assembly configured to fit onto an optically transparent tube having liquid passing therethrough, the in-situ optical monitoring assembly comprising:
a body having one or more surfaces which conform to a contour of an optically transparent tube;
first and second optically transparent windows formed in the one or more surfaces; and
first and second optical components mounted within the body and positioned at the first and second windows, respectively, such that direct line of sight is provided between each of the first and second optical components and an exterior of the body, through respective first and second windows;
wherein:
the first optical component is a light source positioned at the first window;
the second optical component is an optical spectrometer positioned at the second window; and
wherein:
the optically transparent tube comprises a tilted condenser tube provided with insulated walls, a coolant inlet port and a coolant outlet port; and
the in-situ optical monitoring assembly is removably attached to the condenser tube proximate an exit end of the condenser tube such that the optical components of the in-situ optical monitoring assembly are arranged to optically monitor the flowing liquid prior to the liquid exiting the condenser tube.

47. The in-situ optical monitoring assembly according to claim 46, wherein:
the first and second windows are circumferentially spaced apart from one another by a first angular distance of less than 180°.

48. An in-situ optical monitoring assembly configured to fit onto an optically transparent tube having liquid passing therethrough, the in-situ optical monitoring assembly comprising:
a body having one or more surfaces which conform to a contour of an optically transparent tube;

first and second optically transparent windows formed in the one or more surfaces; and first and second optical components mounted within the body and positioned at the first and second windows, respectively, such that direct line of sight is provided between each of the first and second optical components and an exterior of the body, through respective first and second windows; wherein:

the first optical component is a light source positioned at the first window, and configured to emit light at a first wavelength;

the second optical component is a first light detector component positioned at the second window, and configured to collect light in a range of wavelengths which does not include the first wavelength;

the first light detector component comprises an optical spectrometer; and the first and second optically transparent windows are circumferentially spaced apart from one another by a first angular distance less than 180°.

49. An in-situ optical monitoring system configured to monitor a liquid flowing in an optically transparent tube, the system comprising:

an in-situ optical monitoring assembly mounted on an optically transparent tube having liquid passing therethrough, the in-situ optical monitoring assembly comprising:

a body having one or more surfaces which conform to a contour of an optically transparent tube;

first and second optically transparent windows formed in the one or more surfaces, the first and second windows being circumferentially spaced apart from one another by a first angular distance of less than 180°;

a light source positioned at the first window such that a direct line of sight is provided between the light source an exterior of the body, through the first window; and an optical spectrometer positioned at the second window such that a direct line of sight is provided between optical spectrometer and an exterior of the body, through the second window;

an optical control circuit configured to control operation of at least one of light source and the optical spectrometer; and a computer configured to control the optical control circuit.

50. The in-situ optical monitoring system according to claim 49, further comprising a display connected to the computer and configured to display an interface to control an extraction and/or purification process.

51. The in-situ optical monitoring system according to claim 50, wherein the computer and the display are integrated into a single unit.

52. The in-situ optical monitoring system according to claim 51, wherein the optical control circuit is integrated into the single unit.

53. The in-situ optical monitoring system according to claim 51, wherein the optical control circuit is integrated into the optical monitoring assembly.

54. The in-situ optical monitoring system according to claim 49, wherein the optical control circuit is integrated into the optical monitoring assembly.

55. The in-situ optical monitoring system according to claim 49, wherein:

the light source is configured to emit light at one or more wavelengths in the range of 315 to 405 nm; and the optical spectrometer is configured to analyzing fluorescent light collected in the range of 390 nm to 800 nm.

56. The in-situ optical monitoring system according to claim 55, wherein:

the optical spectrometer is configured to analyzing fluorescent light collected in the range of 410 nm to 450 nm.

57. The in-situ optical monitoring system according to claim 56, wherein:

the light source is configured emit light at one fixed wavelength at 365 nm.

* * * * *